(12) United States Patent
Coleman Boone et al.

(10) Patent No.: US 8,998,829 B1
(45) Date of Patent: Apr. 7, 2015

(54) SYSTEM TO ASSESS AMPUTEE PATIENT FUNCTION

(75) Inventors: Kim Lisa Coleman Boone, Seattle, WA (US); David Alan Boone, Seattle, WA (US)

(73) Assignee: Orthocare Innovations LLC, Mountlake Terrace, WA (US)

( * ) Notice: Subject to any disclaimer, the term of this patent is extended or adjusted under 35 U.S.C. 154(b) by 680 days.

(21) Appl. No.: 12/886,374

(22) Filed: Sep. 20, 2010

Related U.S. Application Data

(60) Provisional application No. 61/243,839, filed on Sep. 18, 2009.

(51) Int. Cl.
*A61B 5/11* (2006.01)

(52) U.S. Cl.
CPC ............... *A61B 5/1118* (2013.01); *A61B 5/11* (2013.01)

(58) Field of Classification Search
CPC ...... A61B 5/11; A61B 5/1116; A61B 5/1117; A61B 5/1118; A61B 5/112; A61B 5/1123
USPC ................................................ 600/595, 592
See application file for complete search history.

(56) References Cited

U.S. PATENT DOCUMENTS

| | | | | |
|---|---|---|---|---|
| 5,253,654 A * | 10/1993 | Thomas et al. | ............... | 600/592 |
| 5,323,650 A * | 6/1994 | Fullen et al. | ..................... | 73/172 |
| 5,485,402 A * | 1/1996 | Smith et al. | .................... | 702/160 |
| 5,544,649 A * | 8/1996 | David et al. | .................... | 600/301 |
| 7,396,330 B2 * | 7/2008 | Banet et al. | .................... | 600/300 |
| 7,857,771 B2 * | 12/2010 | Alwan et al. | .................. | 600/595 |
| 7,972,246 B2 * | 7/2011 | Shinomiya et al. | ............... | 482/8 |
| 8,122,772 B2 * | 2/2012 | Clausen et al. | .................. | 73/812 |
| 8,280,679 B2 * | 10/2012 | Maxwell et al. | .............. | 702/160 |
| 2005/0010087 A1 * | 1/2005 | Banet et al. | .................... | 600/300 |
| 2005/0283257 A1 * | 12/2005 | Bisbee et al. | .................... | 623/24 |
| 2006/0142648 A1 * | 6/2006 | Banet et al. | .................... | 600/300 |
| 2006/0195050 A1 * | 8/2006 | Alwan et al. | .................. | 600/595 |

(Continued)

FOREIGN PATENT DOCUMENTS

| WO | WO 2008/093406 | * | 8/2008 | ............. | A63B 71/00 |
|---|---|---|---|---|---|
| WO | WO 2008093406 | * | 8/2008 | ............. | A63B 71/00 |

OTHER PUBLICATIONS

Barth et al. "Gait Analysis and Energy Cost of Below-Knee Amputees Wearing Six Different Prosthetic Feet".*
Gailey et al. "The Amputee Mobility Predictor: An Instrument to Assess Determinants of the Lower-Limb Amputee's Ability to Ambulate," Arch Phys Med Rehabil vol. 83, May 2002.*

(Continued)

*Primary Examiner* — Sean Dougherty
*Assistant Examiner* — Michael C Stout
(74) *Attorney, Agent, or Firm* — Christensen O'Connor Johnson Kindness PLLC

(57) ABSTRACT

A pedometer that records the number of steps over a defined period of time and a moment sensor that records the moments experienced by a prosthesis are used in a networked computer environment to assess the functional activity level and instability of a lower limb amputee. The networked environment may include a user computer and a server computer in communication through the Internet. Both the user computer and the server computer include a functional assessment tool and a stability assessment tool. The tools on the user computer and server computer cooperate in assessing the activity level and the instability of a lower limb amputee. The server computer may further host a Website and a secure online database that provides support to the user including the managing of clients and their medical records.

8 Claims, 20 Drawing Sheets

(56) References Cited

U.S. PATENT DOCUMENTS

| | | | |
|---|---|---|---|
| 2006/0235544 A1* | 10/2006 | Iversen et al. | 623/26 |
| 2008/0140221 A1 | 6/2008 | Macomber | |
| 2008/0278336 A1 | 11/2008 | Ortega | |
| 2009/0240171 A1* | 9/2009 | Morris Bamberg et al. | 600/595 |
| 2010/0035728 A1* | 2/2010 | Shinomiya et al. | 482/8 |
| 2010/0191153 A1* | 7/2010 | Sanders et al. | 600/587 |

OTHER PUBLICATIONS

Gailey, R.S., "Predictive Outcome Measures Versus Functional Outcome Measures in the Lower Limb Amputee," Journal of Prosthetics and Orthotics 18(1S):51-60, Jan. 2006.

* cited by examiner

SYSTEM TO ASSESS AMPUTEE PATIENT FUNCTION

CROSS-REFERENCE TO RELATED APPLICATION

This application claims the benefit of U.S. Provisional Application No. 61/243,839, filed Sep. 18, 2009, which is fully incorporated herein expressly by reference.

BACKGROUND

Advancements in materials have led to a variety of improvements in prostheses, including the use of low weight, high strength materials and energy storage and release components. The variety of choices in prosthesis components is meant to fit with the variety of lifestyles led by lower limb amputees. For example, an elderly person that has a low activity level may not require the most advanced materials. On the other hand, a strong and physically active person may desire a prosthesis that will withstand a more rigorous lifestyle. Both high and low activity prosthesis wearers require that the prosthesis be matched with their lifestyle to ensure that the prosthesis improves their quality of life.

In order to properly assess the activity levels of lower limb amputees, the Medicare program administered by the United States Government has developed an index for assessing an amputee's functional level. The Medicare system of "K" codes provides a set of categories used to distinguish between activity levels of amputees. In the lowest level, K0, the patient does not have the ability or potential to ambulate or transfer safely with or without assistance, and a prosthesis does not enhance their quality of life or mobility. In the next lowest level, K1, the patient has the ability or potential to use a prosthesis for transfers or ambulation on level surfaces at fixed cadence. At the next level, K2, the patient has the ability to traverse low-level environmental barriers such as curbs, stairs, or uneven surfaces. At level K3, the patient has the ability or potential to traverse most environmental barriers and may have vocational, therapeutic, or exercise activity beyond basic ambulation. At the highest level, K4, the patient has the ability or potential for prosthetic ambulation that exceeds basic ambulation skills, exhibiting high impact, stress, or energy levels.

The clinician treating the amputee patient prescribes a prosthesis by assigning the patient to one of the K codes defining the activity level. A problem arises in that there is no objective way to measure activity level. A problem also arises because an overdesigned prosthesis may result in imbalance or instability issues for the wearer too weak to properly control the prosthesis. An underdesigned prosthesis will curtail the lifestyle of an active wearer due to having to compensate for a deficient prosthesis. Both situations usually lead to a reduction in the quality of life and rehabilitation of the patient.

Up until the present time, assessing the functionality of an amputee patient is mostly a subjective evaluation. Based on clinical experience and without any objective tool, some clinicians may decide to underprescribe a prosthesis in order to save on costs or because the clinician does not believe that the patient will be fully rehabilitated to a high functional level. On the other hand, if the clinician overprescribes a prosthesis, the prosthesis is overdesigned and underutilized, thus wasting resources that may be put to better use. In either case, overprescription or underprescription of a prosthesis may diminish the quality of life for the patient, or hamper their rehabilitation because the prosthesis is not correctly fitted.

Accordingly, a tool is necessary to properly assess the functional level of activity of a lower limb amputee.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A first embodiment is related to a system for assessing the activity level of a lower limb amputee. The system includes a pedometer comprising a sensor to determine a step, a clock to keep track of the time period that the pedometer is recording steps and a memory to record the steps and time, a user computer connected to a network in communication with a server computer, wherein the user computer comprises a local functional assessment tool that configures the pedometer to record step data and receives recorded step data from the pedometer; and a server computer in communication with the user computer through a communication network, wherein the server computer comprises a remote functional assessment tool that receives the step data from the user computer and processes the data to provide an activity level of the amputee.

In the first embodiment, the server computer may host a Web site that provides a service for assessing the functional activity level of a lower limb amputee, a client manager tool, and an online database.

In the first embodiment, the remote functional assessment tool may receive inputs of a cadence variability, a potential to ambulate, an ambulation requirement, and a clinical observation to provide the activity level of the amputee.

In the first embodiment, the remote functional assessment tool may provide a value describing a cadence variability as a variance in the amount of time that the amputee spends at a plurality of levels of step rate in a defined period of time.

In the first embodiment, the remote functional assessment tool may provide a value describing a potential to ambulate as a number of steps taken by the amputee in a defined period of time.

In the first embodiment, the remote functional assessment tool may provide a value describing the ambulation requirement as a maximum number of steps taken by the amputee in a defined period of time.

In the first embodiment, the system may further include a docking station connected to the user computer, wherein the docking station communicates with the pedometer.

A second embodiment is related to a method for assessing the activity level of a lower limb amputee executed using one or more computers. The method includes recording the number steps taken by a lower limb amputee over a defined period of time, calculating a first value describing a cadence variability from the recorded steps, calculating a second value describing a potential to ambulate from the recorded steps, calculating a third value describing an ambulation requirement from the recorded steps; and calculating an activity level based on at least, the first, second and third values.

In the second embodiment, the cadence variability is described as a variance in the amount of time that the amputee spends at a plurality of levels of step rate in a defined period of time.

In the second embodiment, the potential to ambulate is described as a number of steps taken by the amputee in a defined period of time.

In the second embodiment, the ambulation requirement is described as a maximum number of steps taken by the amputee in a defined period of time.

In the second embodiment, the method may further include obtaining a fourth value describing a clinical observation of an activity level, and calculating an activity level as the average of the first, second, third and fourth values.

In the second embodiment, the method may further include obtaining at least one descriptor selected from the group consisting of the height of the amputee, the walking speed of the amputee relative to people of similar height, the quickness of stepping by the amputee, the range of walking speeds of the amputee, and the appearance of the leg motion of the amputee, and assigning a cadence setting and response to motion from one or more descriptors.

A third embodiment is related to a method for making a prosthesis. The method includes recording on a computer memory the number of steps taken by a lower limb amputee over a defined period of time, inputting the recorded number of steps into one or more computers and calculating an activity level of a lower limb amputee from the recorded number of steps; and assembling a prosthesis with components that are determined by the calculated activity level.

A fourth embodiment is related to system for assessing the instability of a lower limb amputee wearing a prosthesis. The system includes a moment sensor comprising one or more sensors for determining moments experienced by the prosthesis in the sagittal and coronal planes, a user computer connected to a network in communication with a server computer, wherein the user computer comprises a local stability assessment tool that receives recorded moment data from the moment sensor, and a server computer in communication with the user computer through a communication network, wherein the server computer comprises a remote stability assessment tool that receives the moment data from the user computer and processes the data to provide a stability level of the amputee.

In the fourth embodiment, the server computer may host a Web site that provides a service for assessing the instability level of a lower limb amputee, a client manager tool, and an online database.

In the fourth embodiment, the remote functional assessment tool may receive inputs of moments experienced in the sagittal plane by a prosthesis socket and moments experienced in the coronal plane by a prosthesis socket.

In the fourth embodiment, the remote functional assessment tool may receive a model of alignment derived from a set of training data of sagittal and coronal moments recorded from lower limb prosthesis wearers of a known stability.

A fifth embodiment is related to a method for assessing the instability of a lower limb amputee wearing a prosthesis executed using one or more computers. The method includes recording the sagittal and coronal moments experienced by a prosthesis worn by a lower limb amputee, obtaining a model of stability derived from a set of training data that describes the sagittal and coronal moments recorded from lower limb prosthesis wearers of a known stability, calculating a measure of the instability of the lower limb amputee described as the variance of the recorded moments and the model of alignment.

In the fifth embodiment, a moment sensor coupled to a prosthesis socket may record the sagittal and coronal moments.

In the fifth embodiment, the method may further include downloading recorded sagittal and coronal moments to a user computer in communication with a server computer.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 9 is a representative Web page to create a new account in accordance with one embodiment of the present invention;

DETAILED DESCRIPTION

Disclosed herein is a system and a method for assessing the functional activity level of a lower limb amputee. Also disclosed is a system and a method for assessing the instability of a lower limb amputee wearing a prosthesis.

Figure 1:
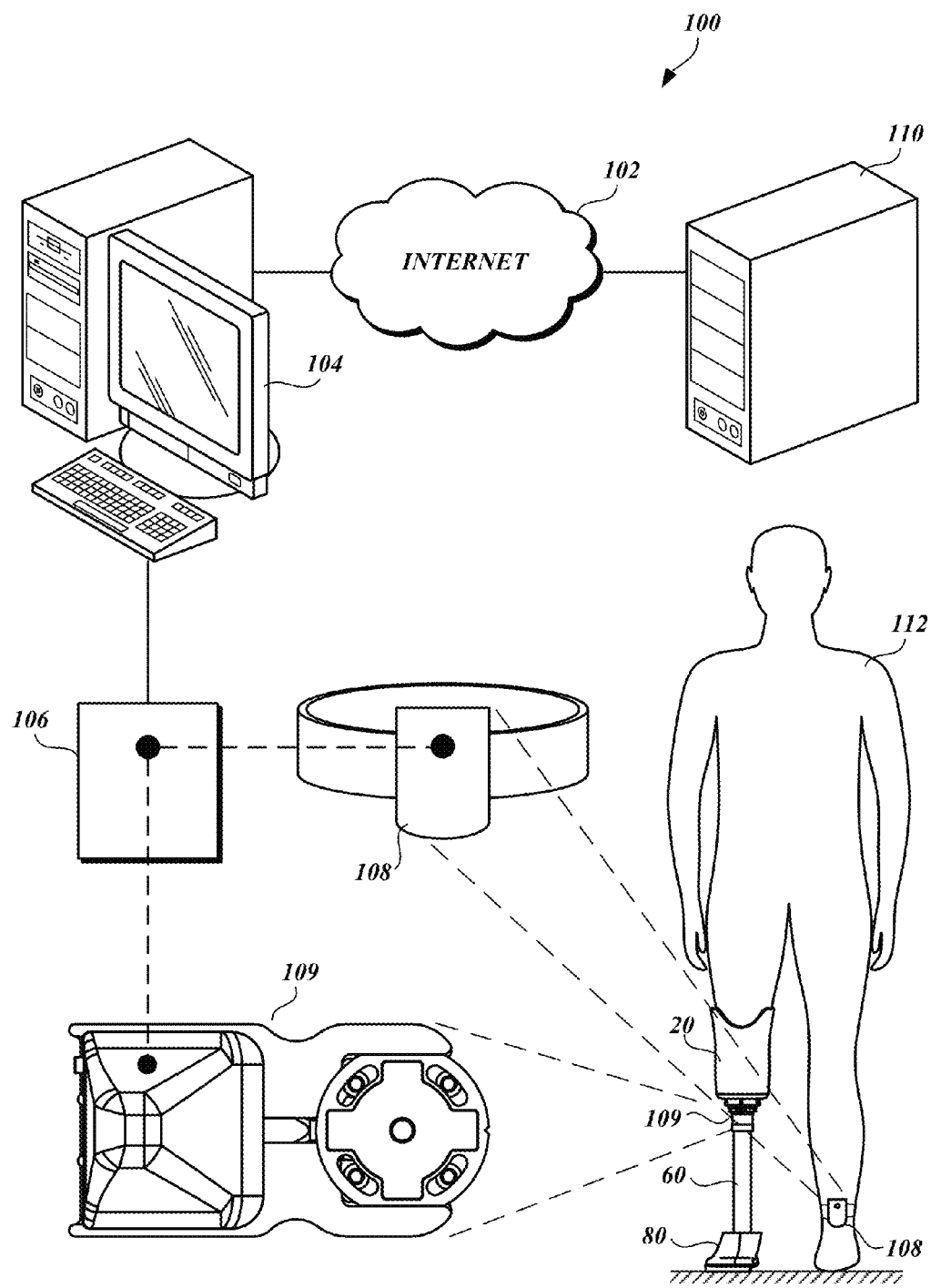
FIG. 1 is a diagrammatical illustration representing one embodiment of an environment in which the present invention is used.

Referring to FIG. 1, a system is illustrated for both assessing the functional activity level and the instability of a lower limb amputee 112 wearing a prosthesis. The system includes a user computer 104 (computer) connected through a communication network, such as the Internet 102, to a server computer 110 (server). The system further includes a docking station 106 (dock) in communication with the computer 104. The system includes a pedometer 108 (step counter). The system includes a moment sensor 109. Either or both of the pedometer 108 and/or the moment sensor 109 may be worn by a lower limb amputee 112.

The pedometer 108 can detect and record the steps the wearer takes over a period of time, and provide the number of steps taken over an interval. During normal walking, a step cycle includes a stance phase when the foot is in contact with the ground and a swing phase when the foot is not in contact. The pedometer 108 is constructed to determine and record the number of steps taken by a wearer during selected time periods. The information is then used to determine a functional level of activity. The pedometer 108 may include an optical transmitter/receiver to permit the pedometer 108 to be optically coupled to the docking station 106 which, in turn, is connected to the computer 104, thereby allowing transmitting information to and receiving information from the computer 104. A suitable pedometer 108 for use in the present invention is described in U.S. Pat. No. 5,485,402, issued to Smith et al., and is fully incorporated herein expressly by reference.

As described in the '402 patent, the pedometer 108 may include a sensor, such as an accelerometer, for providing an acceleration signal indicative of the acceleration of the pedometer 108, which can be correlated to the acceleration of the foot and/or ankle of a wearer. The sensor may also be constructed from a dielectric angle sensor, or a memory switch. Furthermore, the pedometer 108 may comprise multiple sensors for sensing movement relative to one another. The sensor of pedometer 108 provides a signal to a step determination unit. The step determination unit is generally software and hardware responsive to the acceleration or other signal for determining whether the wearer has taken a step. The step determination unit includes a step counter interface coupled to one or more registers. The registers are provided for recording step determination data such as, for example, a minimum acceleration data unit indicating a minimum acceleration required before the activity will be counted as a step, a maximum acceleration data unit indicating a maximum acceleration that will be tolerated before the acceleration signal is discounted, and a minimum time unit indicating the minimum duration that the pedometer 108 must be accelerating before a step will be counted. The pedometer 108 provides the wearer with the ability to program the registers so that the sensitivity of the registers may be more or less in order to increase the accuracy and avoid false positives (step counted when no step taken) and/or false negatives (step taken but not detected). The pedometer 108 includes a memory for storing the step determination data and a clock unit for determining the time period over which the steps are counted. The pedometer 108 includes read-only memory (ROM) for storing program and instruction data for controlling the operation of the data processor computer within the pedometer 108. The pedometer also includes random access memory (RAM) for storing data for programming the data processor as well as for recording data provided by the data processor computer. The memory is also constructed for storing a step rate data unit that indicates the amount of time that the step signal will be ignored after a step is counted. The step rate data unit thereby permits a user to determine a gait, or a step rate (e.g., steps per minute, steps per hour, and the like). To determine the step count data, the data processor counts the number of steps taken during each step rate time interval and records the number into memory. A new step count data unit is provided for each measurement time interval. The measurement time intervals can be consecutive. However, the pedometer 108 may be programmable to specify nonconsecutive time intervals. The length of the measurement time interval may be selected. Additionally, the pedometer 108 can be programmed to begin monitoring at a specific time and end monitoring at a specific time. Alternatively, the pedometer 108 may be programmed to monitor a selected time period of each day for a selected number of days. The pedometer 108 includes a communication interface, such as an optical transmitter/receiver for transmitting and receiving optical signals, circuits for converting the optical signals to electrical signals, and for converting the electrical signals to optical signals. However, the pedometer 108 may employ other means of communicating information to and receiving information from the computer 104. For example, the pedometer 108 may have a wired interface, such as a Universal Serial Bus (USB), or a wireless radio frequency interface, such as Bluetooth. Finally, the pedometer 108 is used to collect step rate data for use in calculating the functional activity level of a lower limb amputee as described further below. When used for the purpose relating to determining the functional activity level, the pedometer 108 can be "locked" to prevent alteration or programming by anyone other than a clinician treating the amputee.

The moment sensor 109 is a device capable of measuring moments (forces tending to rotate an object) experienced by the socket of a prosthesis lower limb. As used herein, "socket" refers to a component of a prosthetic limb into which the residual portion of the living limb that has been amputated fits into. Lower limb amputees may be classified as transtibial, meaning the amputation is below the knee, or transfemoral, meaning the amputation is above the knee. There are other classifications, but these two are the most common. A socket fits over the residual limb. The socket is in turn connected to a prosthetic foot. As can be imagined, the fit and contact between the residual limb and the socket is important for the comfort and stability of the wearer. U.S. Patent Application Publication No. 2008/0139970, issued to Macomber et al., incorporated in its entirety herein by reference, discloses a moment sensor for measuring the moments acting on the socket. The moment measurement information may then be used in calculating an optimal spatial alignment of the prosthesis socket. A prosthesis generally includes at least one articulable component that is adjustable to move the socket forward and backward and side to side to change the spatial alignment of the socket in comparison to the shank and foot. When the prosthesis is out of spatial alignment, walking can be a difficult as forces may push the wearer to either side or forward or backward during every step, thus, fatiguing the wearer quickly as he or she tries to compensate for the misalignment. A spatial alignment is desired that optimizes the comfort and stability of a wearer. An ideal spatial alignment, derived from a training set of data, defines a characteristic curve or sets of curves of moments in the coronal and sagittal planes, plotted from the time the prosthetic foot makes initial contact with the ground through the time the foot lifts off from the ground. The moment sensor 109 is placed on the prosthesis between socket 20 and shank 60, such as at the base of the socket 20, to measure the moments experienced at the socket 20. The moment sensor 109 gathers moment information that tends to bend the prosthesis either to the left or right (coronal plane), or forward or backward (sagittal plane) as the prosthesis is used to walk on the ground. The moment sensor 109 includes four sets of strain gauges placed along the sides of four beams connected to a pylon that experiences the forces from the socket since the pylon connects to the shank, which leads to the foot. As the amputee steps with the prosthesis, the moments experienced at the socket are recorded and may be compared to an ideal model of alignment. The model of alignment is derived from a set of training data that describe the moments of amputees with properly aligned prosthesis. The data collected from a wearer with a misaligned or aligned prosthesis is then compared against the model via the use of statistical algorithms to analyze for closeness between the recorded data and the model. The relationships between the model and the socket moments are known so that it becomes possible to provide instructions to bring a misaligned prosthesis closer to the model.

The moment sensor 109 includes an anterior beam, a posterior beam, a right and a left beam. Each beam further includes a first and second strain gauge attached to the side surface of the beam. Two sets of four strain gauges are arranged into two balanced bridges, each with a passive/resistive temperature component in series with each bridge so as to develop a voltage representative of the total bridge resistance. The orientation of the balanced bridges allows for calculation of moments into two orthogonal planes, such planes being the sagittal plane (anterior/posterior plane) and the coronal plane (right/left plane). The arrangement of the strain gauges in oppositely placed pairs reduces or eliminates the moments experienced along the third (transverse or horizontal) plane orthogonal to the other two. The upper side of the sensor 109 is attached to the bottom of the socket 20 and the bottom side of the sensor 109 is attached to the shank 60. For this purpose, the sensor 109 includes an inverted "pyramid" supported from a hemispherical dome. The sensor 109 rests on a concave matching cup of the shank and so provides articulation of the transverse plane, thus changing the spatial alignment between the socket 20 and the rest of the prosthesis. The moment sensor 109 also includes electrical components to power and convert voltage differences measured by the strain gauges into moments along both the coronal and sagittal planes. Also provided with the moment sensor 109 is a master unit. The master unit may include the power supply, radio transmitter, and/or any other type of wireless communication system, such as optical systems for transmitting and receiving data wirelessly to and from a computer. In this case, a master unit attached to the moment sensor 109 may include optical components that allow the transfer of data to and from the moment sensor 109 to the docking station 106 and computer 104, similar to the pedometer 108. The master unit may include a gyroscope, a central processing unit or computer and a memory to record the moment data gathered while a patient walks along the ground.

Figure 2:
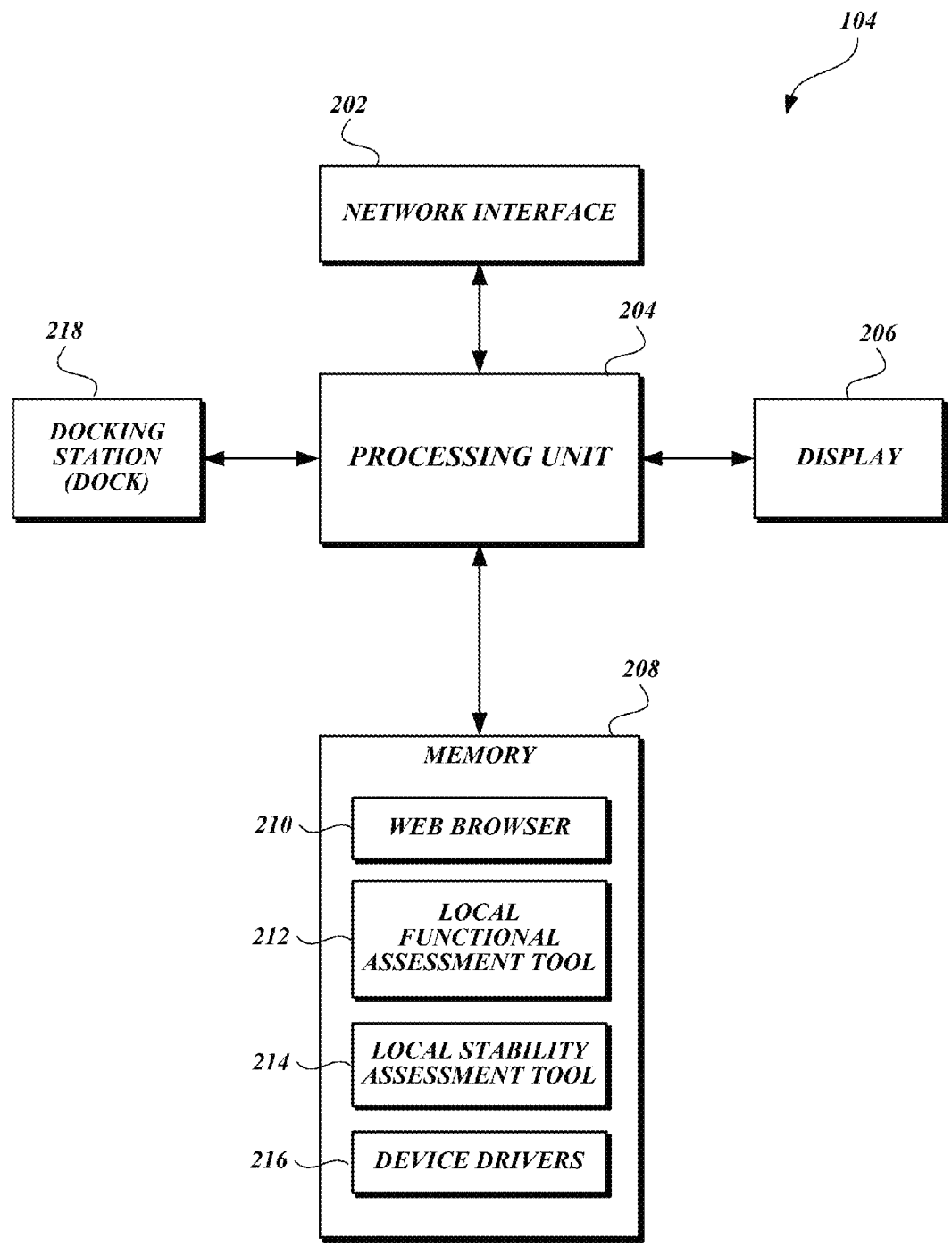
FIG. 2 is a diagrammatical illustration of a representative user computer used in one embodiment of the present invention.

Referring to FIG. 2, the computer 104 includes a processing unit 204, a display 206, a memory 208, and a network interface. The memory 208 generally comprises a random access memory (RAM), a read-only memory (ROM), and a permanent mass storage device, such as a disk drive. The memory 208 stores program code and data necessary for operating a Web browser 210, for running and operating a "local" functional assessment tool 212, for running and operating a local stability assessment tool 214, and various device drivers 216, such as for communicating with the docking station 106. The applications running on the computer may be described in the context of computer-executable instructions, such as program modules being executed by the computer 104. Generally described, program modules include routines, programs, applications, objects, components, data structures, and the like that perform tasks or implement particular abstract data types. "Local" as used herein refers to the computer 104, as opposed to "remote," which describes the server 110. The Web browser 210 can be any Web browser known in the art such as Netscape Navigator® or Microsoft Internet Explorer®. It will be appreciated that the components in the memory 208 may be stored on a computer-readable tangible medium and loaded into the memory 208 of the computer 104 using a drive mechanism associated with a computer-readable tangible medium, such as a floppy or DVD/CD-ROM drive.

The computer 104 is connected to the server computer 110 through a network, such as the Internet 102. As is well understood, the Internet 102 is a collection of local area networks (LANs), wide area networks (WANs), remote computers and routers that use the transmission control protocol/Internet protocol (TCP/IP) to communicate with each other. The World Wide Web (www) is a collection of interconnected, electronically stored information located on servers connected throughout the Internet 102. In accordance with one embodiment disclosed herein, a prosthesis clinician using the computer 104 can assess the functional level of activity and/or stability of a client (amputee) over the Internet 102 via a Web browser by communication to the remote server computer 110 and may pay for receiving a determination and reports relating to a client's functional level and/or stability. The computer 104 can be any number of computer systems, including, but not limited to, work stations, personal computers, laptop computers, personal data assistants, servers, remote computers, etc., that is equipped with the necessary interface hardware connected temporarily or permanently to the Internet 102. Those of ordinary skill in the art will appreciate that the computer 104 could be any computer used by a prosthesis clinician to communicate with the remote server 110 to send and receive information relating to a client's functional activity level or stability. Additionally, those of ordinary skill in the art will appreciate that the computer 104 may include many more components than those shown in FIG. 2. However, it is not necessary that all of these generally conventional components be shown in order to disclose an illustrative embodiment for practicing the present invention. For example, the computer 104 may include an operating system, such as the Windows® operating system. As shown in FIG. 2, the computer 104 includes a network interface 202 for connecting to a LAN or WAN, or for connecting remotely to a LAN or WAN. Those of ordinary skill in the art will appreciate that the network interface 202 includes necessary circuitry for such a connection, and is also constructed for use with the TCP/IP protocol, the particular network configuration of the LAN or WAN it is connecting to, and a particular type of coupling medium. The computer 104 is also connected to the docking station 218 via any communication protocol compatible with both the computer 104 and the docking station 218.

Figure 3:
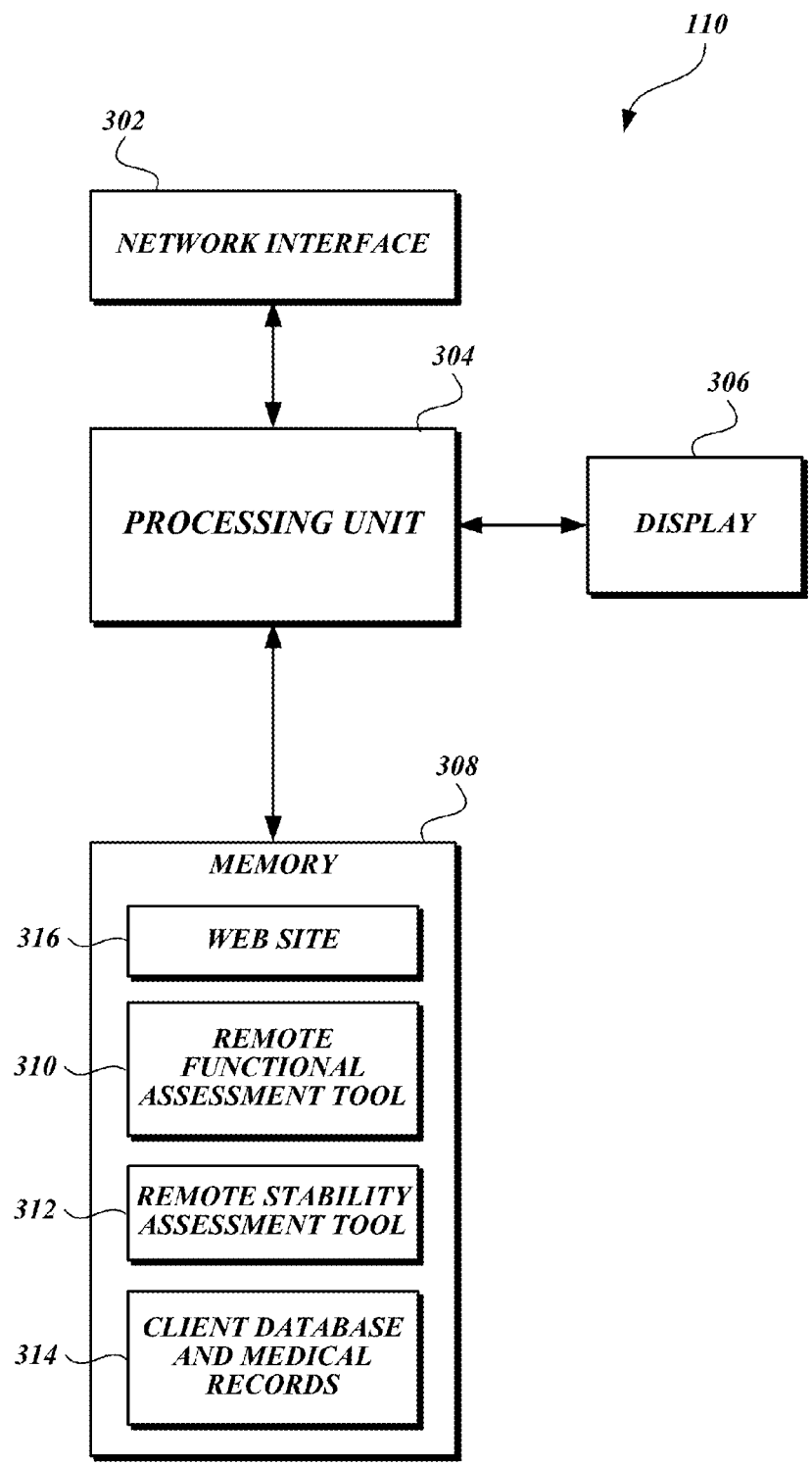
FIG. 3 is a diagrammatical illustration of a representative server computer used in one embodiment of the present invention.

FIG. 3 shows the various components of the server computer 110. Those of ordinary skill in the art will appreciate that the server 110 includes many more components than those shown in FIG. 3. However, it is not necessary that all of these generally conventional components be shown in order to disclose an illustrative embodiment of practicing the present invention. As shown in FIG. 3, the server 110 includes a network interface 302 for connecting to a LAN or WAN, or for connecting remotely to a LAN or WAN. Those of ordinary skill in the art will appreciate that the network interface 302 includes necessary circuitry for such a connection, and is also constructed for use with the TCP/IP protocol, the particular network configuration of the LAN or WAN it is connecting to, and a particular type of coupling medium. The server 110 includes a processing unit 304, a display 306, and a memory 308. The memory 308 generally comprises a random access memory (RAM), read-only memory (ROM), and a permanent mass storage device, such as a hard disk drive, tape drive, optical drive, floppy disk drive, or combination thereof. In one embodiment, the memory contains a client and medical records database 314 which includes information relating a list of patients and each patient's medical records, including, but not limited to, step data and stability data and other information and associated reports. The server 110 memory may host a Web site containing a multiplicity of Web pages. The Web site provides a Web service to allow users to manage the medical records of amputee clients, and specifically to determine the functional activity level and instability or stability of lower limb amputees. The memory 308 also contains a remote functional assessment tool 310. "Remote" as used herein is used to denote components found on the server 110, and "local" is used to denote components found on the computer 104. The remote functional assessment tool 310 receives input step data and processes the data and outputs a functional level of activity of a lower limb amputee client. Also included in the memory 308 is a remote stability assessment tool. The remote stability assessment tool 312 receives stability data (i.e., moment data), processes the moment data, and provides a level of instability (or stability) of a lower limb amputee client.

Communications between the computer 104 and the server computer 110 may be encrypted via the generation of an encryption key pair comprising a secret key and a public key. For example, a secure socket layer (SSL) protocol is used for establishing a secure connection. SSL uses public key encryption incorporated into the Web browser 210 and server 110 to secure the information being transferred over the Internet 102. The encryption, decryption and transmission of encrypted data over the Internet 102 using a public and private key is a well know operation.

Having described the components of a system used to assess the functional activity level and instability of a lower limb amputee client, a method to both assess the functional activity level and instability will be described.

Figure 4:
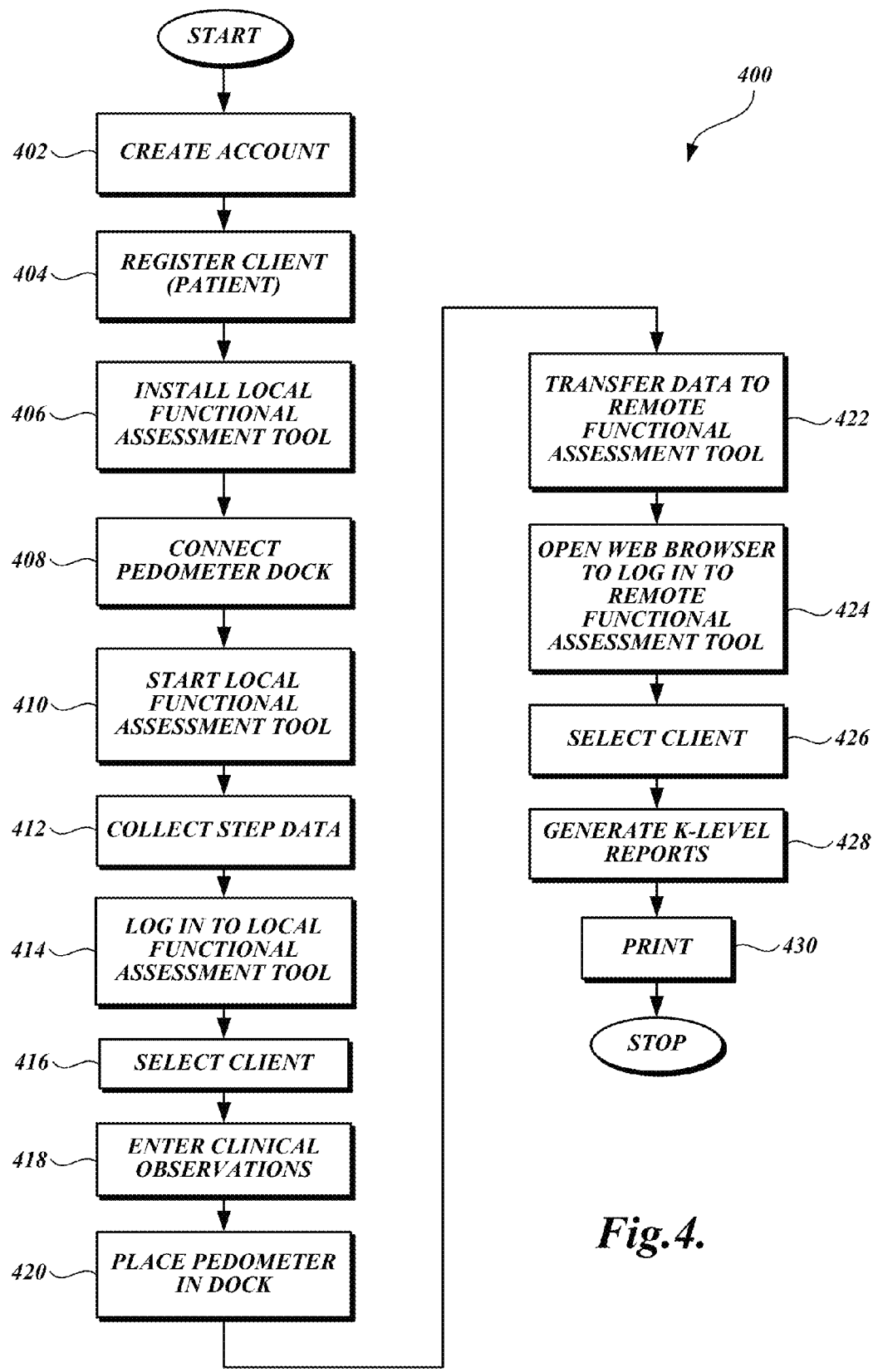
FIG. 4 is a flow diagram of a method to determine functional activity level of a lower limb amputee client in accordance with one embodiment of the present invention.

Referring to FIG. 4, a method 400 for assessing the functional activity level of a lower limb amputee is illustrated. Assessing the functional activity level is important since knowing the activity of the client is useful in prescribing the appropriate type of components that will be used in manufacturing the prosthesis. For example, a high level activity indicates that a prosthesis needs to be built with certain components, such as energy storage/release capability, as well as lighter, stronger components. A low functional activity level indicates the client may require a prosthesis that does not include such components. The functional activity level assessment as disclosed herein uses the pedometer 108 to gather data relating to the number of steps over a specific time interval. The data is then arranged into specific time intervals to show a histogram of the number of steps in each interval. "Step" as used herein refers to the act beginning with placing the heel of the foot on the ground through the lifting of the toe or foot off the ground.

The disclosed method uses the system illustrated and described in FIG. 1. The system uses a pedometer 108, a suitable pedometer is the one described in U.S. Pat. No. 5,485,402, incorporated herein by reference in its entirety. However, other pedometers capable of keeping track of the number of steps and time intervals may be used. The system may include the docking station 106 that can optically receive the data collected by the pedometer 108 and communicate the data to the computer 104. However, in other embodiments, the pedometer may communicate directly with the computer 104 or even the server 110 through the Internet. The computer 104 communicates via the Internet 102 with the server 110 to provide the data collected with the pedometer 108 and receives results from the server 110 using the local and remote functional assessment tools 212 and 312 stored in the computer 104 and the server 110, respectively. The server 110 provides a service in the form of hosting a Web site to store the list of clients, the clients' medical records, including the data collected using the pedometer 108 and moment sensor 109, provide for the assessment of the activity level and instability of clients, generate reports, provide for the creation of accounts, provide for the downloading of the local functional assessment tool, and collect payment for the use of the service. The local functional assessment and stability assessment tools 212, 214 perform such activities as device setup and data reading in connection with the pedometer 108 and moment sensor 109. The remote functional assessment and stability assessment tools 310, 312 perform functions such as online remote storage of step and moment data, medical data and processing the step and moment data, and presenting the results through a Web site for consumption and analysis. The remote functional and stability assessment tools 310, 312 also offer the ability to manage client information. Most of the functionality resides on the Web site and can be accessed through the Web browser 210. This allows the local functional and stability assessment tools 212, 214 to remain small and easy to install and be used on most of the commonly used computer platforms. All the communications between the local functional and stability assessment tools 212, 214 and the server 110, as well as between the Web browser 210 and the Web site is encrypted, thus providing for security. The data is securely stored on the server 110. A clinician will only have access to the information that they themselves entered into the system. This is managed by creating accounts for each of the clinicians.

Figure 8:
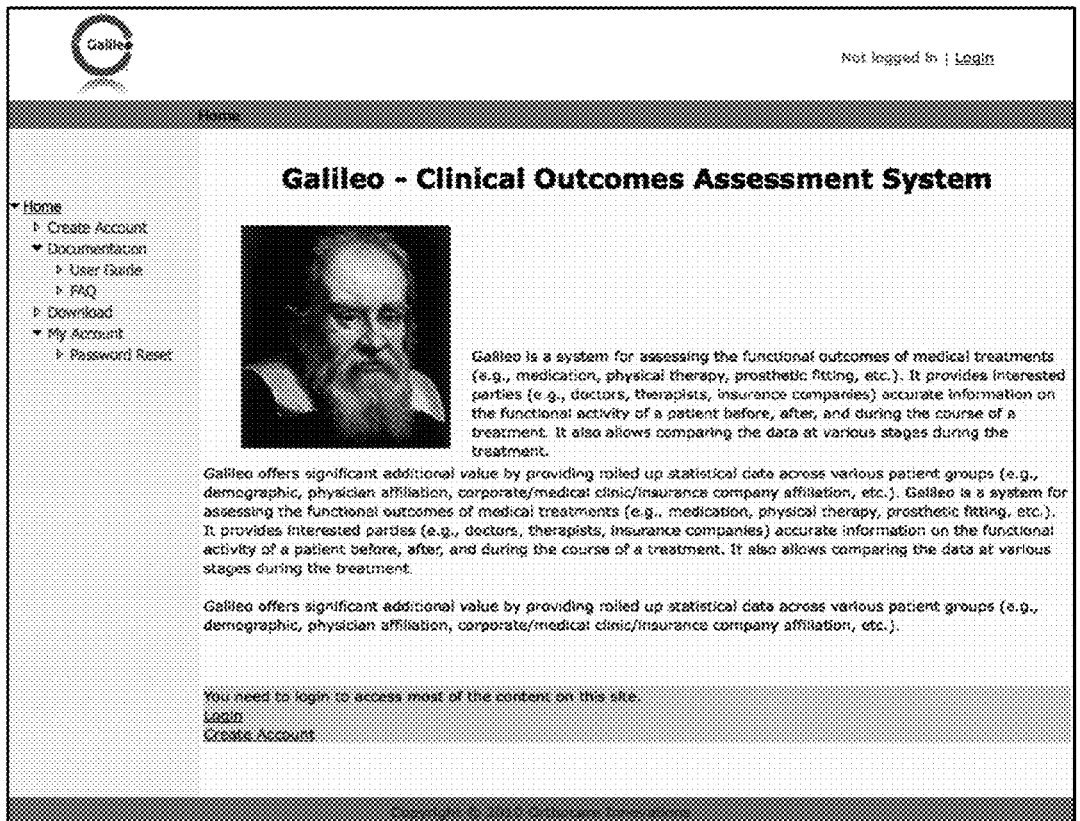
FIG. 8 is a representative home Web page of a Web Site in accordance with one embodiment of the present invention.
Figure 9:
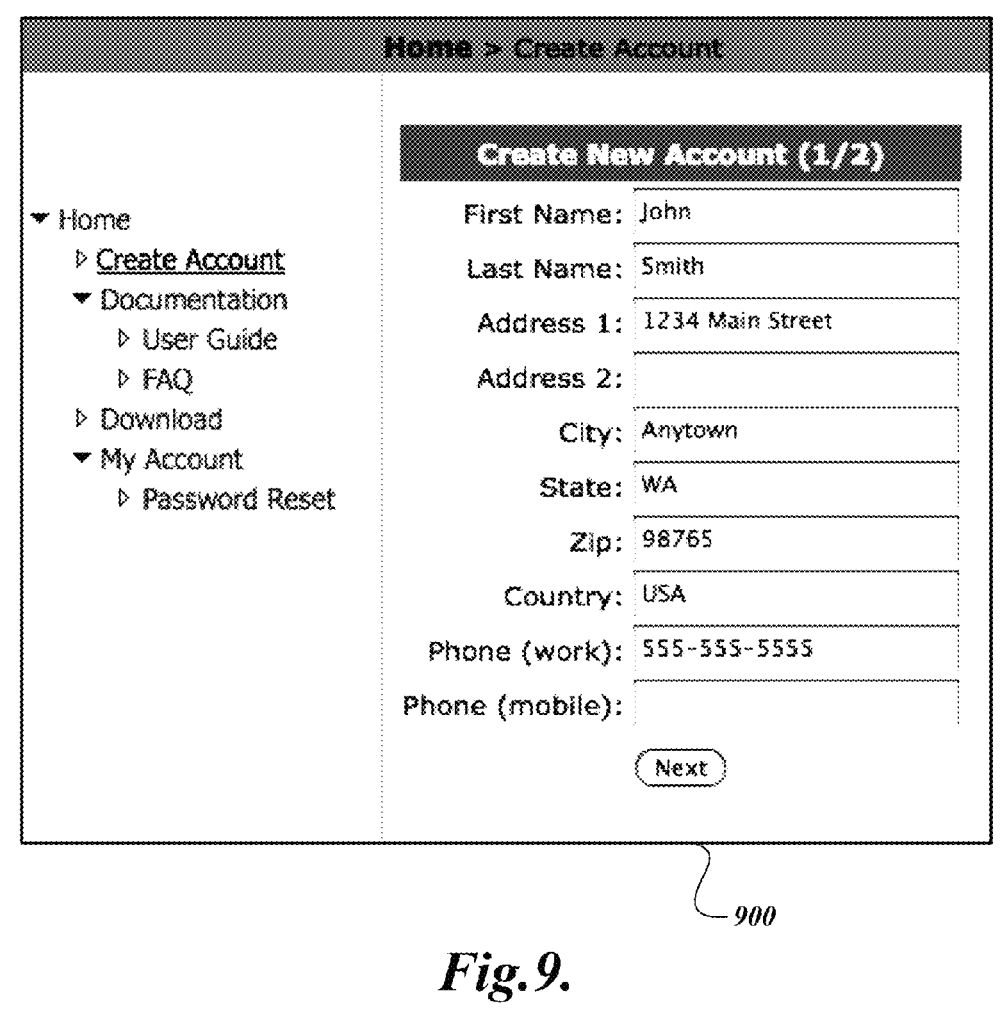

Referring now to FIG. 4, which illustrates a method for determining the functional activity level of lower limb amputee, step 402 is for creating a user account to use a Web site for determining the functional activity level and instability of a lower limb amputee client. The user, a clinician for treating amputee clients, begins by opening the Web browser 210 on the computer 104 and navigates to a particular Web site that supports a Web service for assessing the functional activity level and/or stability of lower limb amputee clients. The server 110 may host the Web site. FIG. 8 is a representative Web page 800 that may be displayed in order for the first-time user to create an account. The Web page includes a menu item entitled "Create Account." The user moves a pointer or a cursor over the menu item "Create Account" and selects it. Upon selecting the "Create Account" item, a Web page may be displayed, such as the Web page 900 illustrated in FIG. 9. The Web page 900 of FIG. 9 requests personal information.

Figure 10:
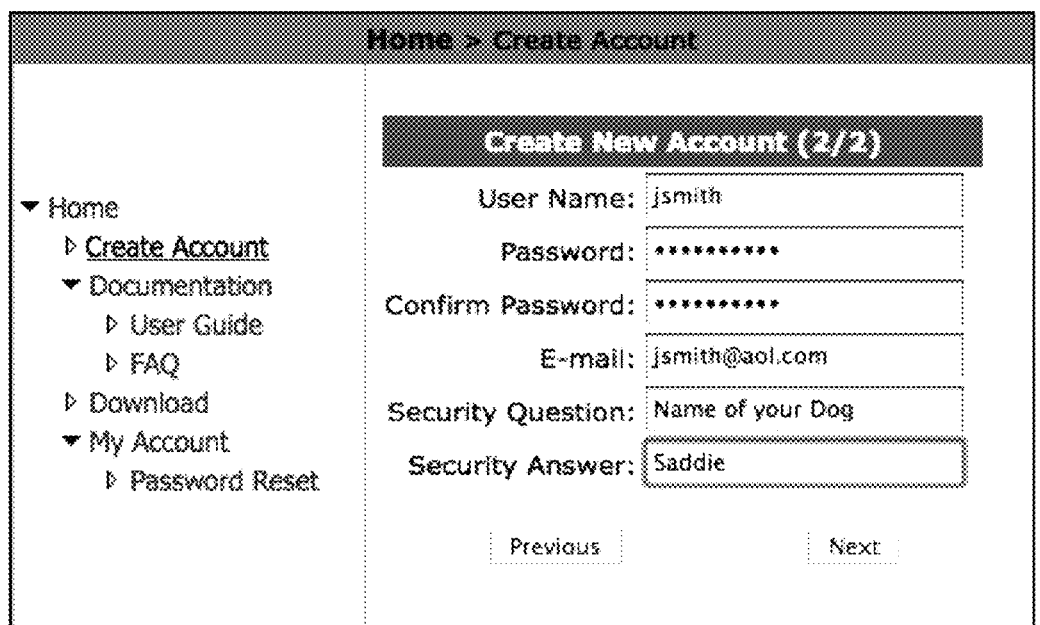
FIG. 10 is a representative Web page to create a new account in accordance with one embodiment of the present invention.
Figure 11:
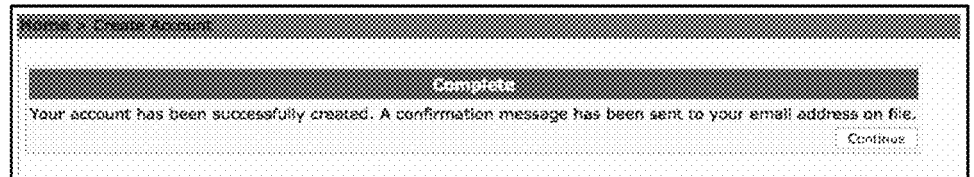
FIG. 11 is a representative notification that a new account has been successfully created in accordance with one embodiment of the present invention.

Some of the information may be optional and can be edited at a later point in time. After entering the required and/or optional information, the user moves the pointer to the "Next" button and selects it. After selecting the "Next" button, a Web page may be displayed, such as the Web page illustrated in FIG. 10. In the Web page 1000, the user will select a user name and password. In one embodiment, once the user name is chosen, the user name cannot be changed later. Preferably, a strong password is chosen that is case sensitive, contains a minimum of seven characters and at least one non-alphanumeric character. The user is prompted to enter an e-mail address that is unique to the Web site. The Web site checks and verifies that the e-mail is unique. After completing registration, the user will be presented with a successful account creation notice, such as the message 110 illustrated in FIG. 11, and an e-mail confirming the account creation may be sent to the e-mail address.

Figure 12:
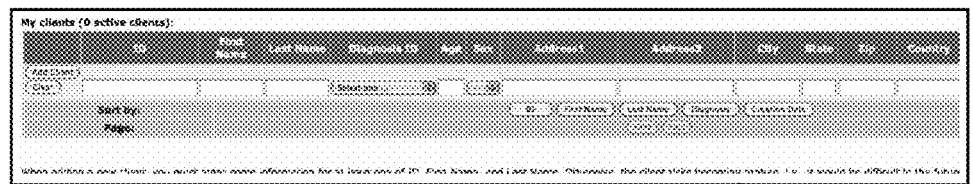
FIG. 12 is a representative Web page to enter client data into an online database in accordance with one embodiment of the present invention.

Referring to FIG. 4, from block 402, the method enters block 404. Block 404 is for the user to enter client information. Using the Web browser, the user navigates to a Web page that includes a menu including the option to "Manage Clients" from the "Data Management" group. Upon selection of the "Manage Clients" item, a Web page such as the Web page 1200 of FIG. 12 may be displayed. The user can enter information corresponding to each client for which they plan to enter step or moment data. The user may enter the personal information of the client in each field. After the information is added to the data input fields, the user may move the pointer over the "Add Client" button and select it. After selecting the button, the client will be added to the online database 314 in server 110. The Web page 1200 allows for clearing all the information at once by moving the pointer over the "Clear" button and selecting it. The Web page 1200 also allows for sorting clients by ID number, first name, last name, diagnosis, and creation date by moving the pointer over the respective button and selecting it.

Data entered up to this point in the method relates to the creation of a user account and to the creation of a list of an online client database. In order to begin collecting the step data that will be used to calculate the functional activity level, the user is required to load the local functional assessment tool onto the user computer 104. It is common practice to download applications by establishing a connection to the Internet 104 and then downloading the application onto the user computer 104. From step 404, the method enters step 406. In step 406, the user can download and install the local functional assessment tool from the Web site 316 and configure the computer 104 to operate the docking station 106. Part of the installation may include installing device drivers needed to communicate with the docking station 106 and a serial port driver, such as USB. The docking station 106 may be physically connected to the computer 104 through a USB cable. The computer 104 has an operating system such as the Windows® operating system. The operating system may automatically detect the connection to a new device and search for the appropriate device driver. From step 406, the method enters step 408, for connecting the pedometer dock.

Figure 13:
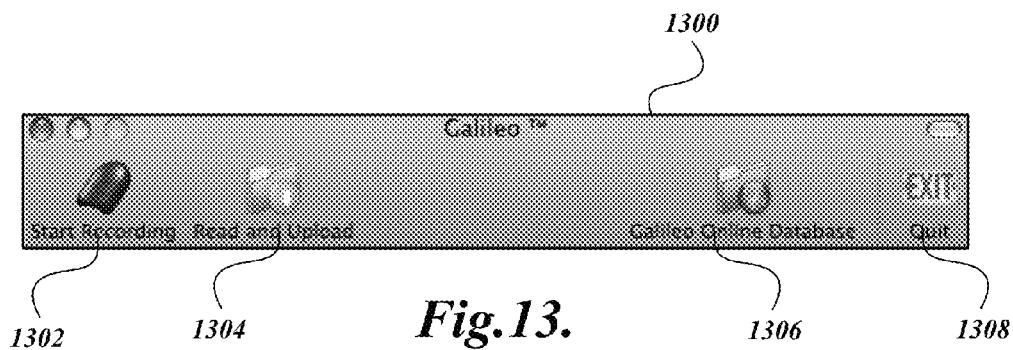
FIG. 13 is a representative graphical user interface of a local functional assessment tool in accordance with one embodiment of the present invention.
Figure 14:
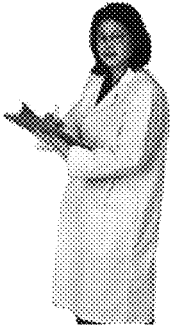
FIG. 14 is a representative window of a local functional assessment tool for entering client information in accordance with one embodiment of the present invention.
Figure 15:
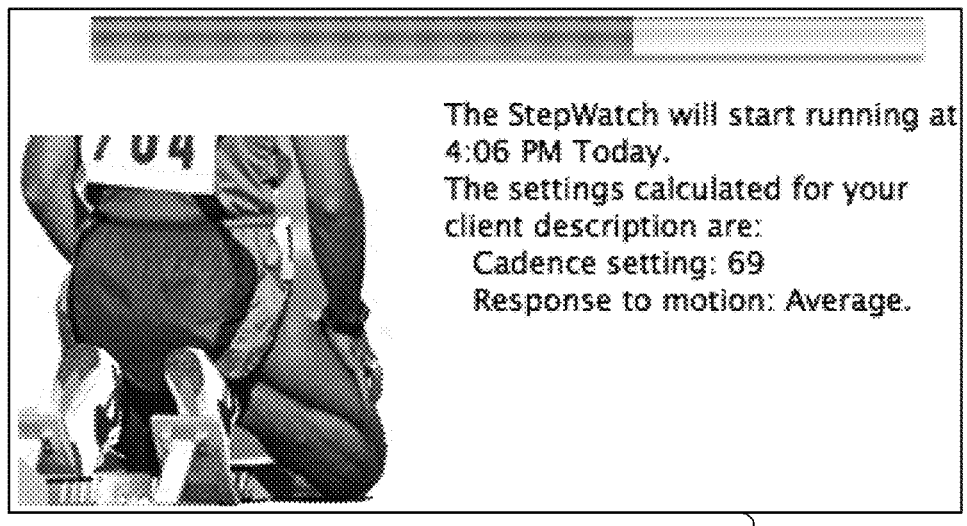
FIG. 15 is a representative window of the local functional assessment tool to notify of start time and recording parameters in accordance with one embodiment of the present invention.
Figure 16:
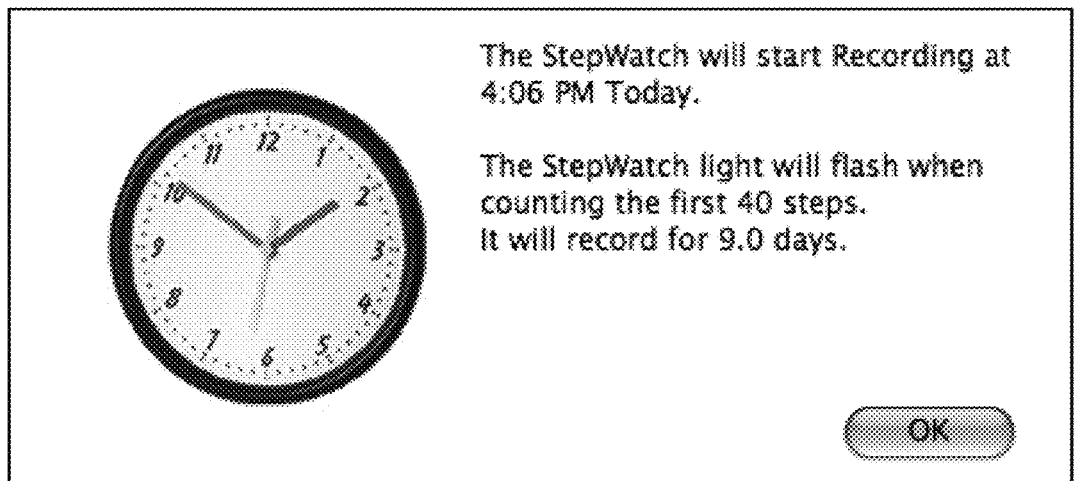
FIG. 16 is a representative window of the local functional assessment tool to notify of the start time and recording parameters in accordance with one embodiment of the present invention.

After the hardware and software are installed and configured, the user may then start the local functional assessment tool in step 410. As part of the installation of the local functional assessment tool, an icon may be generated that appears on the computer screen. Moving the pointer over the icon and selecting it will start the local functional assessment tool 212. A window, such as the window 1300 illustrated in FIG. 13, may appear on the display of the computer 104 when the local functional assessment tool is started on the computer 104. The window represents a graphical user interface of the local functional assessment tool that may include a "Start Recording" icon 1302, a "Read and Upload" icon 1304, an "Online Database" icon 1306, and a "Quit" icon 1308. Selecting the "Start Recording" icon 1302 starts a process for configuring and setting up the pedometer 108 and dock 106 to program the pedometer 108 with instructions regarding the start time and stop time of the recording interval or intervals. Selecting the "Read and Upload" icon 1304 starts a process for retrieving the information from the pedometer after the step data has been collected. Selecting the "Online Database" icon 1306 starts a process for navigating to a Web site containing secure client medical records, including the step data and moment data and associated reports. Selecting the "Online Database" icon 1306 will start the Web browser 210 to interface with the remote server 110 that stores the database. Selecting the "Quit" icon 1308 quits the local functional assessment tool 212 and closes the window 1300. As discussed above, preferably, the pedometer 108 is programmable to receive instructions concerning the duration and intervals over which steps are to be recorded, including the start and the stop times. In step 410, the user starts the local functional assessment tool 212 to begin the process of recording of data. The user may move the pointer over the "Start Recording" icon and selecting it. The user may be prompted to place the pedometer 108 in the docking station 106 and verify that he or she has done so by selecting an "Okay" button. The functional assessment tool verifies that pedometer 108 is configured for recording data. After verification, a window may be displayed, such as the window 1400 illustrated in FIG. 14. The window 1400 may prompt the user to provide information such as, client height, whether the client engages in quick stepping, such as participating in sports, dancing, etc., the walking speed of the client relative to people of similar height, the range of speeds, and leg motion. Representative choices for walking speed are "Slow," "Fast," and "Normal." The user may select one. Representative choices for range of speeds are "Uses a moderate range of speeds," "Regularly uses both extremes," and "Rarely varies pace." The user may select one. Representative choices for leg motion that describe the appearance of the client's leg motion are "Normal," "Fidgety or Dynamic," "Gentle or Geriatric," and "Severely Impaired." The user may select one. For each entry, the user may be provided with a menu providing a limited range of answers. The choices selected are used to adjust the sensitivity of the pedometer 108 to acceleration of the leg, both in magnitude and duration. Once all the information is entered, the user may move the pointer over the "Start" button and select it. The local functional assessment tool 212 will then download the instructions to the pedometer 108 through the docking station 106. While the local functional assessment tool 212 is downloading instructions to set up the pedometer 108, a progress notification may appear on a window, such as the window 1500 illustrated in FIG. 15. The window 1500 will indicate such information as the time the pedometer 108 will start to record data and the particular settings of the client. Once the pedometer 108 setup is completed, a confirmation window may be displayed such as the window 1600 illustrated in FIG. 16, showing the time the step recording will begin and the duration of the recording.

From step 410, the method enters step 412. During step 412, the client collects the data. The pedometer 108 may be worn by the client continuously, day and night, for the selected period of time. During this period, every time the client completes a step, the pedometer 108 will count the step and may note the time interval in which it was recorded.

Additionally, the time may also be recorded. After the recording period is at an end, the client may return the pedometer 108 to the user clinician.

Figure 17:
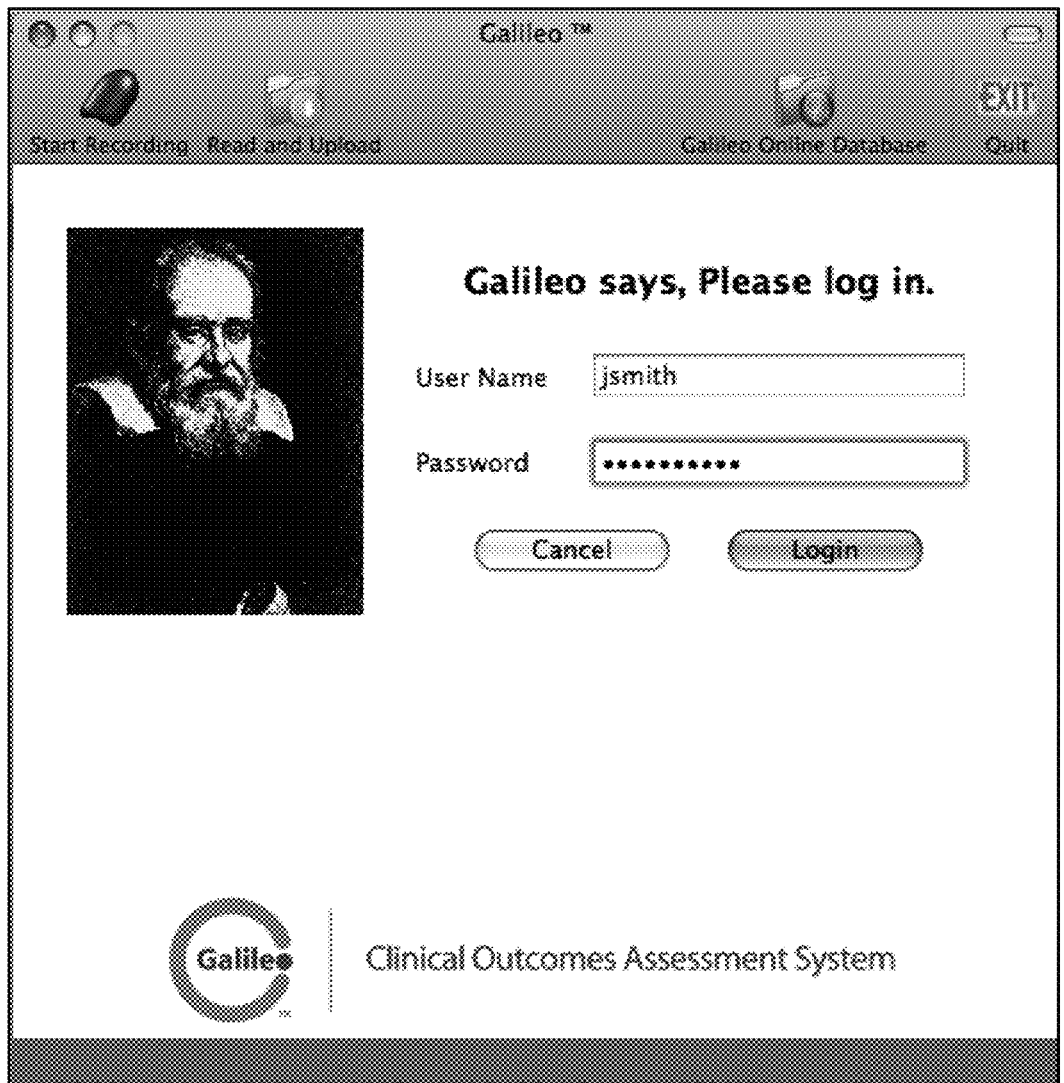
FIG. 17 is a representative window to log into a Web site in accordance with one embodiment of the present invention.
Figure 18:
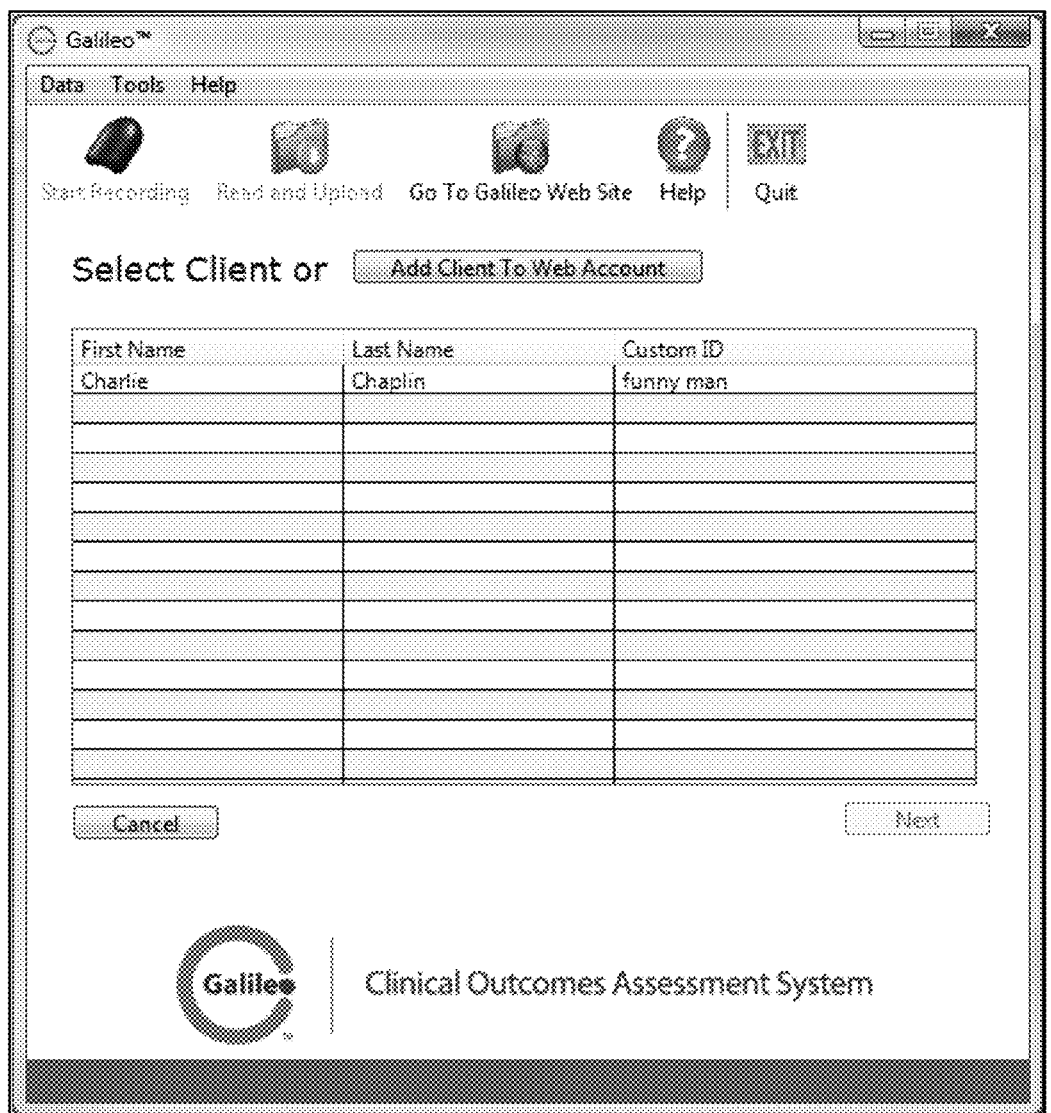
FIG. 18 is a representative Web page to display the client database in accordance with one embodiment of the present invention.

From step 412, the method enters step 414. Step 414 is for logging into the system to begin downloading the data to the online database 314. Once the patient has worn the pedometer 108 for the selected period of time and has returned the pedometer, the data may be downloaded from the pedometer 108 and uploaded to the Web site 316. This process is carried out using the computer 104 connected to the Internet 102 and the local functional assessment tool 212. The pedometer 108 may be placed alongside the dock 106 to enable optical communications from the pedometer 108 to the dock 106. The user may once again start the local functional assessment tool 212 by selecting an icon on the desktop of computer 104. The user may select the local functional assessment tool icon and a window, such as the window 1300 illustrated in FIG. 13, may be displayed. The user moves the pointer over the "Read and Upload" icon 1304 and selects it. This will bring up a window to log in, such as the window 1700 of FIG. 17. The local functional assessment tool 212 will ask the user to log into the system using the previously created account. The user enters the user name and password for the account. After successfully logging in, the list of clients that have been previously registered may be displayed on a window such as the window 1800 illustrated in FIG. 18. In step 416, the user moves the pointer over the selected client whose data is to be uploaded. If the client is not in the database, a new client may be created by moving the pointer over the "Add Client To Web Account" button and selecting it. The same procedure as described before for adding a new client will start.

Figure 19:
FIG. 19 is a representative Web page for collecting clinical observations in accordance with one embodiment of the present invention.
Figure 20:
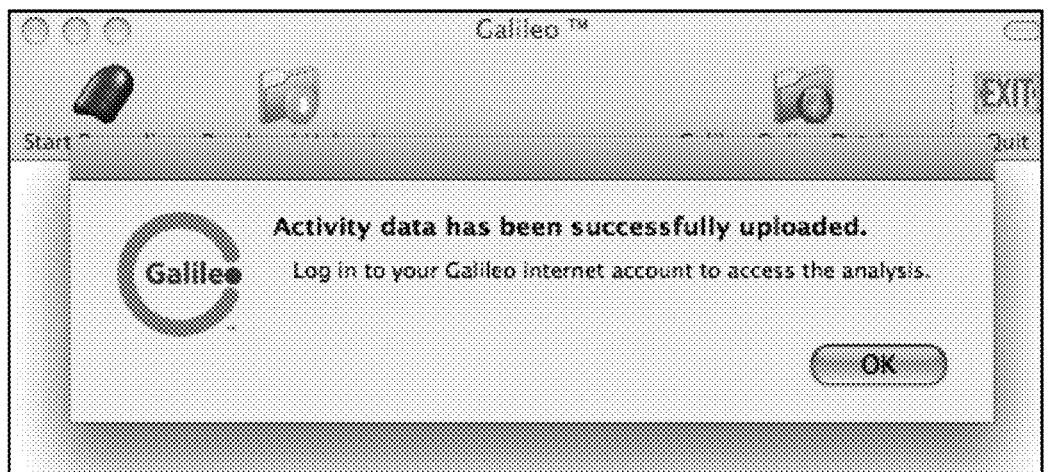
FIG. 20 is a representative notification indicating that step data has been successfully uploaded to the remote server in accordance with one embodiment of the present invention.

After the user selects a client, the user can move the pointer over the "Next" button and select it. Step 418 is for entering clinical observations. In step 418, the local functional assessment tool 212 will ask the user to enter the client's weight and the user's assessment of the functional activity level of the client. In the United States, the functional levels have been assigned designations K0 through K4. While the discussion of the functional activity levels of lower limb amputees is stated in terms of K levels, it should be readily apparent that other designations can be used according to the present invention. A window, such as the window 1900 illustrated in FIG. 19, may be displayed for this purpose. Once the fields are populated, the user may move the pointer over the "Next" button and select it. Upon selecting the "Next" button, the user will be asked to confirm that the pedometer 108 has been placed on the dock 106. Step 420 is for placing the pedometer 108 alongside the dock 106. The functional assessment tool 212 may prompt the user to verify the correct placement of the pedometer 108. Once the user confirms the pedometer 108 is correctly placed on the dock 106, step 422 is entered for reading the data and transmitting the data over the Internet 102 to the remote server 110. When the data upload is complete, the user may be notified the data transfer has been successfully completed by displaying a notification window, such as the window 2000 illustrated in FIG. 20.

Figure 21:
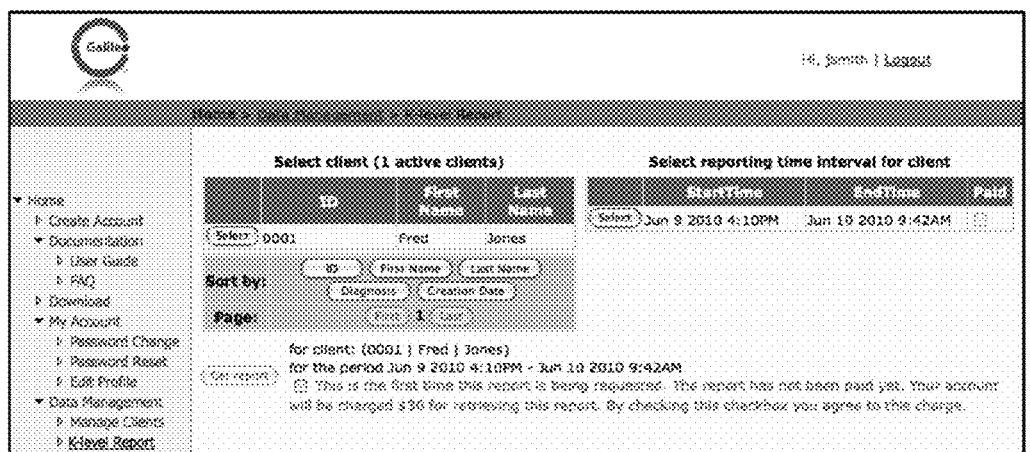
FIG. 21 is a representative Web page to manage clients in accordance with one embodiment of the present invention.

From step 422, the method enters step 424. Step 424 is for opening the Web browser to log onto the Web site 316 associated with the remote functional assessment tool 312. The local functional assessment tool 212 may be used to open the Web browser to communicate to the server 110. The user navigates via a Web browser to log into the Web site 316 to gain access to the remote functional assessment tool. The user logs into the Web site 316 using the same user name and password as the local login. A Web page, such as the Web page 2100 illustrated in FIG. 21, may be displayed to the user on the computer 104. To receive an assessment of the functional activity level, the user moves the pointer over the "K-level Report" menu option under the "Data Management" group in the left side of the Web page 2100. This will bring up the list of active clients. The user moves the pointer over the name of the client about whom the user desires to receive a report. The client may have a plurality of data sets that have been uploaded for various time periods. The user will be able to distinguish among the data sets based on the recording interval or dates. The user has the option of selecting the time interval for which to receive a report.

Figure 22:
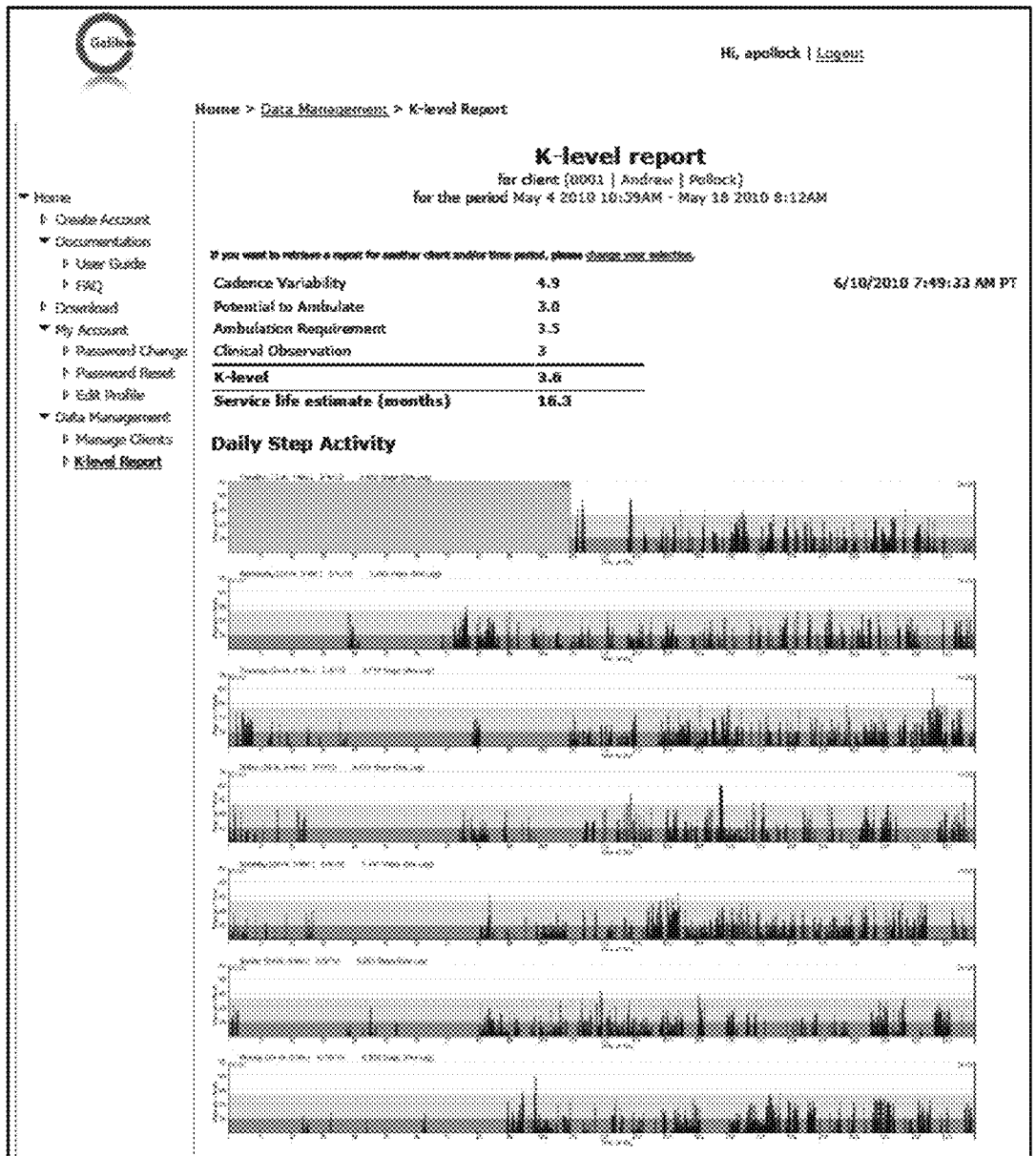
FIG. 22 is a representative Web page to report the activity level of a lower limb amputee.

The first time a particular report is requested, the user may have to pay a user fee to receive the report. If the user has not paid for a report, a checkbox under the "Paid" column of the report will not be checked, and the "Get Report" feature may be disabled and shown grayed out. The Web page will ask the user to explicitly agree to the charges for the cost of the report. Transactions involving payment in exchange for goods over the Internet has become a common channel for providing goods to users of such goods. The Web site 316 disclosed herein uses any of the secure forms of payment for such transactions. Following the initial payment for a report for one data set, for example, the user will be able to access the report at any time in the future for no additional charge. After selecting an "Agreement" checkbox, the "Get Report" feature will be active. The user can move the pointer over the button and select it to retrieve the report. The Web page 2200 illustrated in FIG. 22 shows a representative functional activity level report. The Web page 2200 may include options for printing and saving the report.

The remote functional assessment tool uses four descriptors to calculate a functional activity level (K-values in the report). The different descriptors used for the functional activity level (K-level) determination are: cadence variability, potential to ambulate, ambulation requirement, and clinical observation. The number reported for each represents how a client, for a particular monitoring session, matches up versus ADL requirements and other clients in the database. The ADL requirements are defined by a number of common activities of daily living, such as cooking, cleaning, commuting, and working. It is normal for a client to score higher in some categories than others and each of the four descriptors gets an equal "vote" as to the ultimate reported K-value. The system uses an equal vote because the client is not penalized for their particular requirements. For instance, cadence variability scores equally with ambulation requirement. Also, the measures are "continuous" variables. That is, the remote functional assessment tool 312 calculates how the descriptor maps to the K-level in $\frac{1}{10}$th increments. This gives the measure much more sensitivity to the condition and change of the patient. A patient with a measure of 2.7 is really a 2 rising to 3, or a 3 falling, etc.

The remote functional assessment tool 312 calculates cadence variability as the variance in the amount of time that the client spends at three levels of step rate (0-15 steps/minute, 15-40 steps/minute, and 40+ steps/minute). These ranges of step rates are representative of different kinds of activity. The rates are then mapped to a database of representative activities of K1 through K4 prosthesis users. For example, the recorded step data is compared statistically to a sample of previously measured amputee activities in order to categorize the rates as reflecting the previously measured activities of others. This will be used to provide a number.

The second descriptor, potential to ambulate, is calculated by monitoring the prosthesis continuously, such as a week, for example. If the data shows step activity during the week, this is an indication of potential to ambulate even if the activity is not sustained. For example, the peak activity is selected over a short period of time, such as several minutes (5 minutes in one embodiment), whenever it may occur throughout the interval monitored. This may be compared statistically to a sample of previously measured amputees in order to arrive at a number. No step activity would be seen if the person is completely unable to ambulate at the time, but it is effective with patients returning to function. In either occasion, it comprises one vote and is averaged out by the clinical observation.

The clinical observation is the input entered during step 418 of the method. If the user is confident that the patient can return to a K4 level, but the potential measured at the time is K2, then, the result of their potential comes out as K3, which is probably a reasonable place to start if the patient is currently unable to walk with a normally varied cadence. The clinical observation provides an activity level based generally known method of assessing an activity level. The method disclosed herein uses such number and provides additional descriptors calculated from step data to provide a more objective assessment.

The fourth descriptor, ambulation requirement, looks at the maximum number of steps the person will take with their prosthesis during a 20-minute window whenever it occurs throughout the day. The amount of sustained use of the prosthesis is an accurate indicator of whether they have need to transfer, ambulate in the home, ambulate in the community, or have needs in excess of ADL. Once a value is received for each of the four descriptors, the values are added and divided by four to arrive at the average value, which is reported as the K-level of activity in the report. As can be appreciated, the reported level of activity is based on measured step data performed by the client over an extended period of time and can provide a more reliable value as opposed to a purely clinical assessment.

Figure 6:
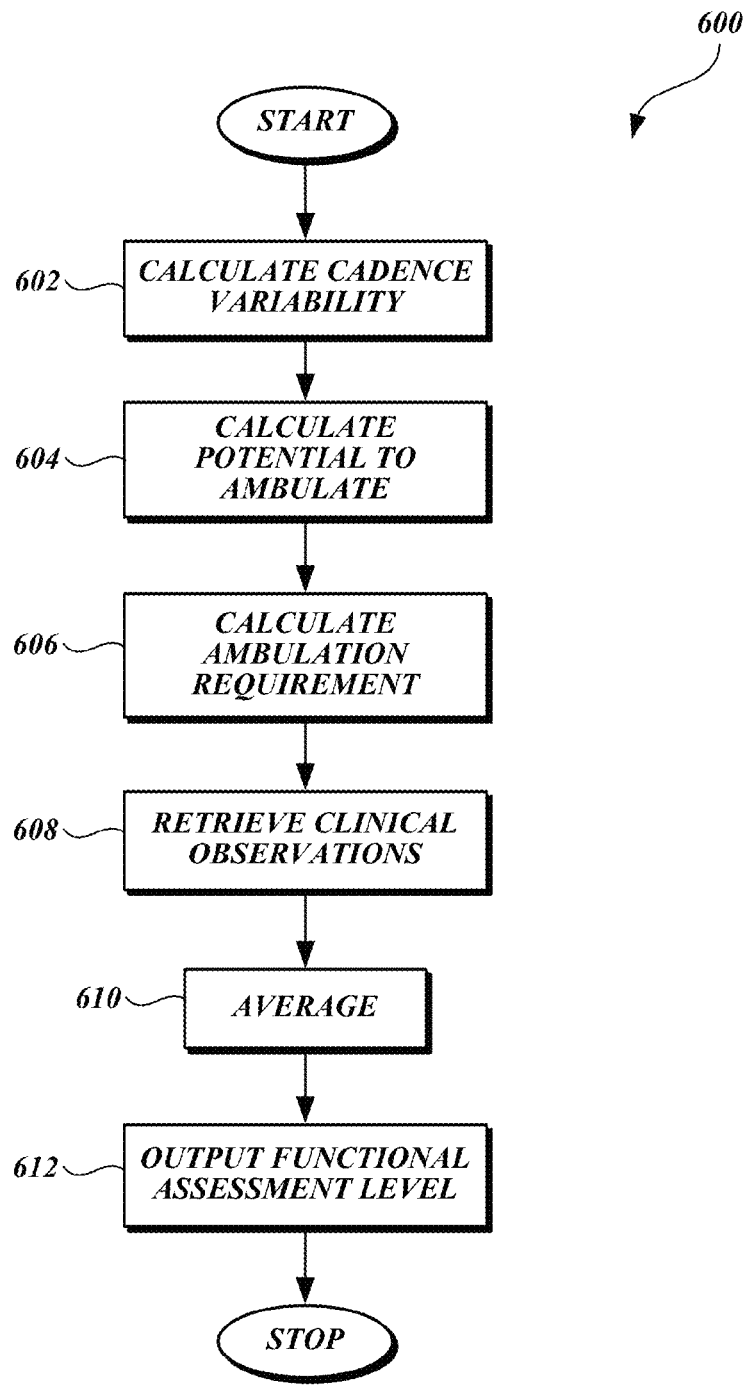
FIG. 6 is a flow diagram of a method for determining functional activity level from step data in accordance with one embodiment of the present invention.

Referring to FIG. 6, a method 600 is illustrated for the calculation of the functional activity level. As mentioned above, functional activity levels for lower limb amputees in the United States are measured by assigning a K value, from K0, no activity, to K4, as defined in the Background section of this application. In step 602, the system calculates the cadence variability. From step 602, the system enters block 604. In block 604, the method calculates potential to ambulate. From step 604, the method enters step 606. In step 606, the method calculates the ambulation requirement. From step 606, the method enters step 608. In step 608, the method retrieves the clinical observation of the K level. From step 608, the method enters step 610 to average the four previous inputs valued from greater than 0 to 4. The average is the reported functional activity level in step 612.

As discussed above, the computer 104 and remote server 110 may include both a functional assessment tool as well as a stability assessment tool.

Figure 5:
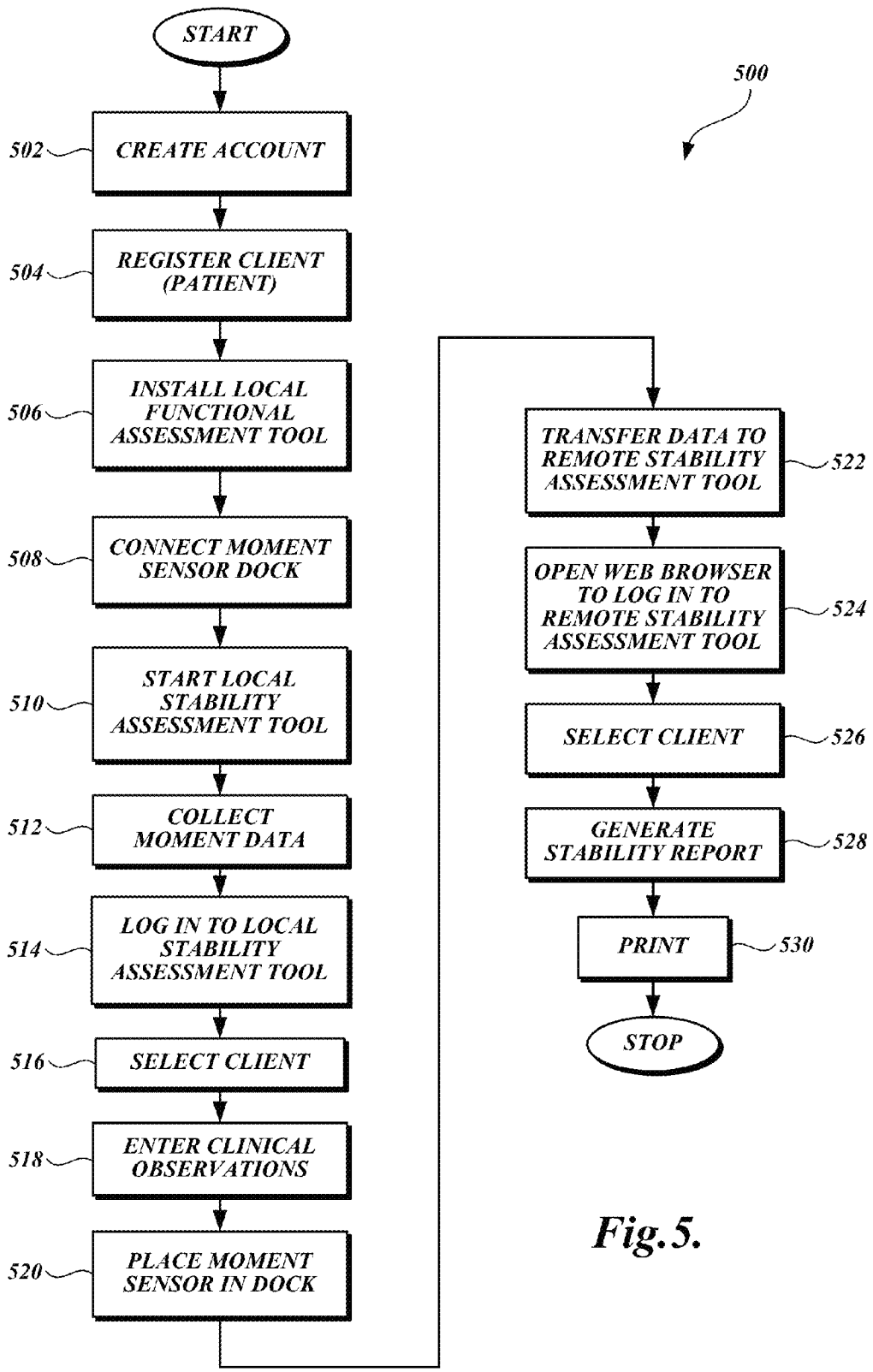
FIG. 5 is a flow diagram of a method to determine stability of a lower limb amputee client in accordance with one embodiment of the present invention.

Referring to FIG. 5, a method for calculating the instability (or stability) of a lower limb amputee is illustrated. Stability an instability may be viewed as the same in this disclosure. The method illustrated in FIG. 5 uses the moment sensor 109 to collect data in place of the pedometer 108 that collects step rate data. Accordingly, the method illustrated in FIG. 5 employs many similar steps as the method illustrated in FIG. 4. The difference between the methods being that to obtain a measure of instability, the data collected is moment data measured for the length of one or more steps. As discussed above, a step as used herein refers to the period from the time that the prosthesis foot makes contact with the ground to the time the prosthesis foot is lifted off from the ground. The moments that act in the coronal and sagittal planes on the prosthesis socket during each step are collected and recorded in the memory of the moment sensor 109.

Figure 7:
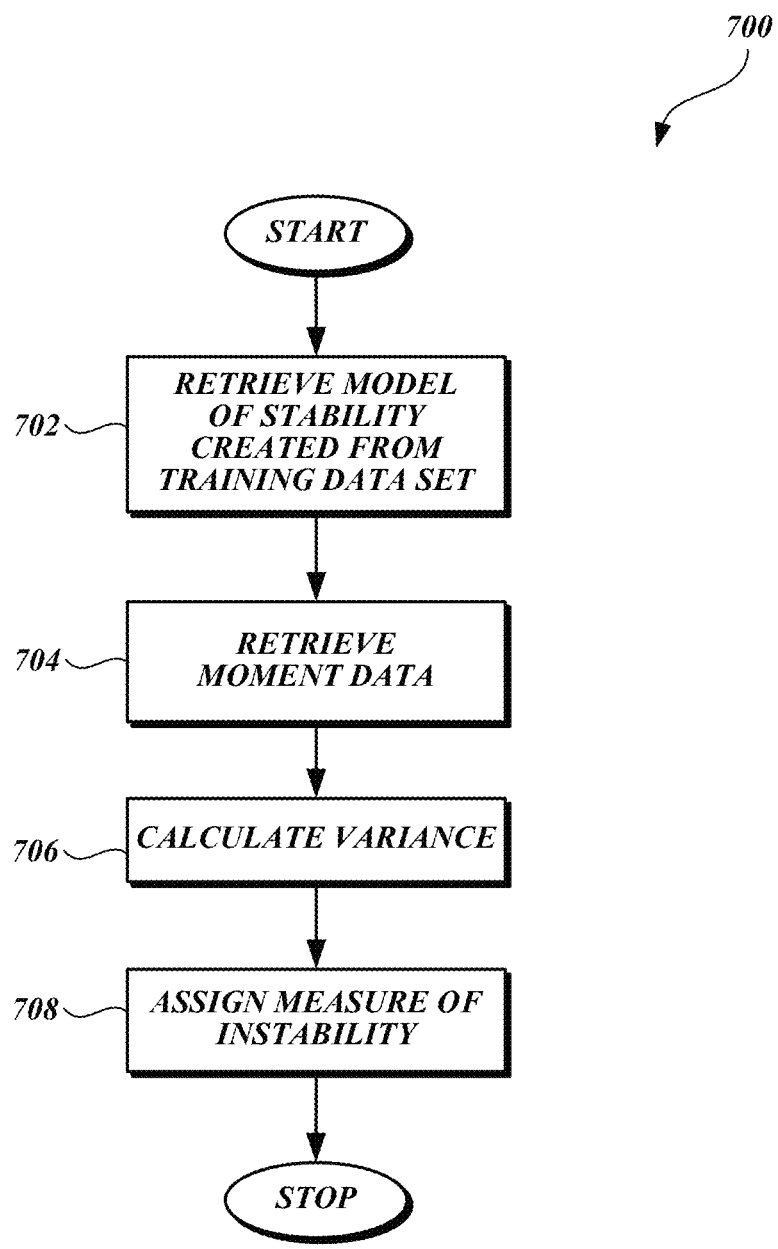
FIG. 7 is a flow diagram of a method for determining the stability from moment data in accordance with one embodiment of the present invention.

In step 512 of method 500, moment data is collected instead of step rate data. The moment sensor 109 communicates via the same or different docking station 106. The moment data that is collected is for the calculation of instability. Referring to FIG. 7, a method is illustrated for calculating the stability of a lower limb amputee patient.

Figure 23:
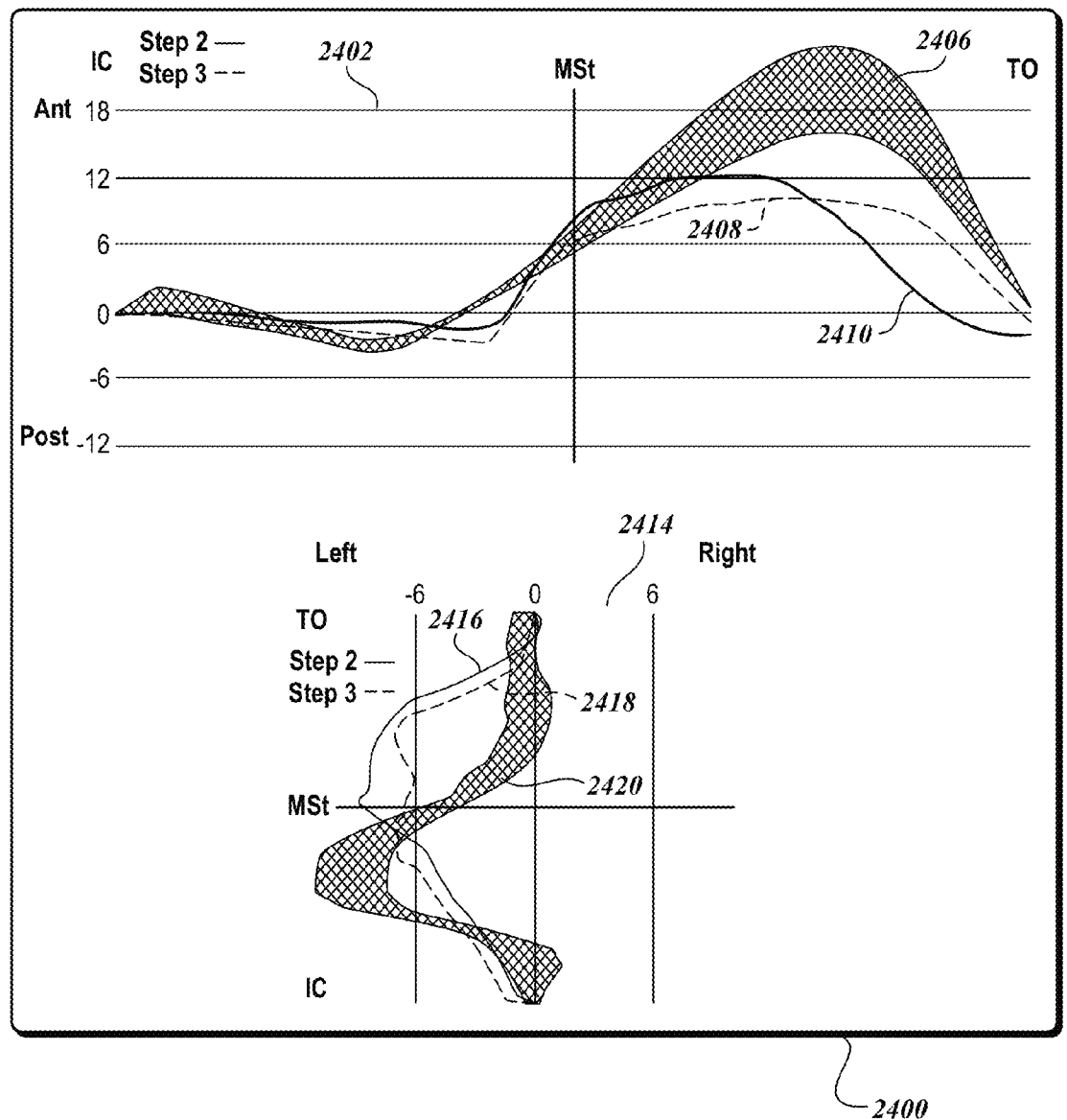
FIG. 23 is a graphical representation of a model of stability plotted against data collected for a step in both the coronal and sagittal planes.

In block 702, the method retrieves a model of stability created from a training data set. Referring to FIG. 23, a graphical representation of a model of stability is illustrated by the shaded areas 2406 and 2420 denoting the acceptable range of moments for stability in the anterior/posterior (sagittal) plane 2402 and the right/left (coronal) plane 2414. Moments are plotted for two steps in both the coronal and sagittal planes from the time of initial contact (IC) of the foot to the toe off (TO) from the ground. One embodiment for deriving a model of stability is by using a training data set collected from a plurality of lower limb amputees with known stabilities. Stability can be expressed as a coefficient of variance of the mediolateral movement over time during the stance phase of gait. The ideally stable prosthesis patients are permitted to walk to collect moment data representative of the ideal stability profile. After testing numerous ideally fitted prostheses, the data is collected and used to create the model of stability. Statistical methods are known for creating models that describe the ideal behavior from large amounts of data. Another simplified method is to collect moment data from the patient with a prosthesis that is ideally fitted to the patient and with which the patient can walk stably. This moment data then becomes the standard to which all future prosthesis must conform to be classified as stable.

From step 702, the method enters step 704. In step 704, the method retrieves actual moment data of the client being analyzed for instability. Referring to FIG. 23, the actual moment data represented by lines 2408 and 2410 I the sagittal plane and lines 2416 and 2418 in the coronal plane may not lie within the boundaries of the model of stability 2406 and 2420. The lines on the anterior/posterior plane and left/right planes illustrate that there may be deviations of the actual moment data from the model.

Instability is then a measure of the deviation or variance of the actual data from the model. To analyze for instability, the analysis may take certain "gait" variables into consideration. Gait variables are characterizations of information gathered during the step motion. Gait variables may include, but are not limited to some or all of the anterior/posterior moment and right/left moment at each 20% increment in time of the step phase, the maxima and minima of the anterior/posterior moments and the right/left moments for the first and last 50% of the step phase, the slope of the change in anterior/posterior moment and right/left moment during each successive 20% time increment, the integrated anterior/posterior moment and right/left moment measured over the period of each step phase. One or more of these gait variables are then applied to the model of stability using a statistical analysis tool.

The equations used in deriving the model of stability are derived heuristically to minimize an external criterion called the prediction error sum of squares, or PESS, for previously measured socket moments.

$$PESS = 1/N \sum_{t=1}^{N} (y_t - f(x_t, \hat{a}_t))^2 \quad (1)$$

Where N is the number of gait variable samples available, Y is the target stability, and a is an estimation of the combined parameters that describe the instability. The equation derivations are achieved using the group method of data handling described by Madala and Ivakhnenko (Madala, H., and A. Ivakhnenko, "Inductive Learning Algorithms for Complex Systems Modeling," CRC Press, Boca Raton, Fla., U.S.A., 1994), fully incorporated herein expressly by reference. Solving the derived model equations with the gait variables results in a numeric estimation of the instability. For robustness, estimations from each of the equations become a vote added to a more generalized estimation of the stability. Stability is signified by decreased variability in step to step movement sessions time plots. A unit less (nondimensional) index number can be assigned based on population statistics.

After conclusion of the functional level assessment and/or the instability assessment, the user has information from which to prescribe a prosthesis matching the activity level or instability of the user. For example, after calculating an activity level of 4, the user may prescribe a prosthesis having lightweight, high strength materials for use in building the prosthesis. Also, a foot having an energy storage/release component may also be prescribed. On the other hand, if the functional assessment level is a 1, the user may prescribe a prosthesis having less exotic materials, such as stainless steel or aluminum materials, and basic unmodified rubberized materials as the foot with minimal energy storage/release capability. The method for determining stability assists the clinician to track the progress of an amputee to determine whether the amputee's progress is increasing to decreasing.

While illustrative embodiments have been illustrated and described, it will be appreciated that various changes can be made therein without departing from the spirit and scope of the invention.

The embodiments of the invention in which an exclusive property or privilege is claimed are defined as follows:

1. A system for assessing the activity level of prescribing the components of a prosthesis to a lower limb amputee, comprising:
    a pedometer comprising a sensor to determine a step, a clock to keep track of the time period that the pedometer is recording steps and a memory to record the steps and time;
    a user computer connected to a network in communication with a server computer, wherein the user computer comprises a local functional assessment tool that configures the pedometer to record step data and receives recorded step data from the pedometer; and
    a server computer in communication with the user computer through a communication network, wherein the server computer comprises a remote functional assessment tool that receives the step data from the user computer and processes the data to provide a value determinative of a functional ability of the amputee, wherein the value of the functional ability is an average derived from a value representing cadence variability, a value representing potential to ambulate, a value representing ambulation requirement, and a value representing a clinical observation.

2. The system of claim 1, wherein the server computer hosts a Web site that provides a service for assessing the functional activity level of a lower limb amputee, a client manager tool, and an online database.

3. The system of claim 1, wherein the remote functional assessment tool provides the value describing a cadence variability as the variance in the amount of time that the amputee spends at a plurality of levels of step rate in a defined period of time.

4. The system of claim 1, wherein the remote functional assessment tool provides the value describing the potential to ambulate as a number of steps taken by the amputee in a defined period of time.

5. The system of claim 1, wherein the remote functional assessment tool provides the value describing the ambulation requirement as a maximum number of steps taken by the amputee in a defined period of time.

6. The system of claim 1, further comprising a docking station connected to the user computer, wherein the docking station communicates with the pedometer.

7. The system of claim 1, wherein the server computer further provides a value that is determinative for a prescription of components for a prosthesis.

8. The system of claim 1, wherein the value representing cadence variability or the value representing potential to ambulate includes a comparison of the step activity compared to a sample of amputees.

* * * * *